US009078900B2

(12) United States Patent
Kuzma et al.

(10) Patent No.: US 9,078,900 B2
(45) Date of Patent: Jul. 14, 2015

(54) IMPLANTABLE DEVICE FOR THE DELIVERY OF RISPERIDONE AND METHODS OF USE THEREOF

(75) Inventors: Petr Kuzma, Princeton, NJ (US); Harry Quandt, Bensalem, PA (US)

(73) Assignee: BRAEBURN PHARMACEUTICALS BVBA SPRL, Brussels (BE)

( * ) Notice: Subject to any disclaimer, the term of this patent is extended or adjusted under 35 U.S.C. 154(b) by 123 days.

(21) Appl. No.: 12/569,558

(22) Filed: Sep. 29, 2009

(65) Prior Publication Data
US 2010/0080835 A1 Apr. 1, 2010

Related U.S. Application Data

(60) Provisional application No. 61/101,548, filed on Sep. 30, 2008, provisional application No. 61/117,448, filed on Nov. 24, 2008.

(51) Int. Cl.
A61K 9/00 (2006.01)
A61P 25/18 (2006.01)
A61K 31/519 (2006.01)

(52) U.S. Cl.
CPC ............. *A61K 31/519* (2013.01); *A61K 9/0024* (2013.01); *A61K 9/0092* (2013.01)

(58) Field of Classification Search
None
See application file for complete search history.

(56) References Cited

U.S. PATENT DOCUMENTS

| | | | |
|---|---|---|---|
| 3,948,254 A | 4/1976 | Zaffaroni | |
| 3,975,350 A | 8/1976 | Hudgin et al. | |
| 3,993,073 A | 11/1976 | Zaffaroni | |
| 4,131,604 A | 12/1978 | Szycher | |
| 4,136,145 A | 1/1979 | Fuchs et al. | |
| 4,207,809 A | 6/1980 | Brill | |
| 4,207,890 A | 6/1980 | Mamajek et al. | |
| 4,386,039 A | 5/1983 | Szycher | |
| 4,469,671 A | 9/1984 | Zimmerman et al. | |
| 4,523,005 A | 6/1985 | Szycher | |
| 4,720,384 A | 1/1988 | DiLuccio | |
| 4,743,673 A | 5/1988 | Johnston et al. | |
| 4,751,133 A | 6/1988 | Szycher et al. | |
| 4,933,182 A | 6/1990 | Higashi et al. | |
| 5,035,891 A | 7/1991 | Runkel et al. | |
| 5,207,705 A | 5/1993 | Trudell et al. | |
| 5,254,662 A | 10/1993 | Szycher et al. | |
| 5,266,325 A | 11/1993 | Kuzma et al. | |
| 5,292,515 A | 3/1994 | Moro et al. | |
| 5,354,835 A | 10/1994 | Blair | |
| 5,626,862 A | 5/1997 | Brem et al. | |
| 5,629,008 A | 5/1997 | Lee | |
| 5,728,396 A | 3/1998 | Peery et al. | |
| 5,756,632 A | 5/1998 | Ward et al. | |
| 5,789,411 A | 8/1998 | Gooberman et al. | |
| 5,958,317 A | 9/1999 | Aguadisch | |
| 5,980,927 A | 11/1999 | Nelson et al. | |
| 6,113,938 A | 9/2000 | Chen et al. | |
| 6,287,295 B1 | 9/2001 | Chen et al. | |
| 6,313,254 B1 | 11/2001 | Meijs et al. | |
| 6,375,978 B1 | 4/2002 | Kleiner et al. | |
| 7,067,116 B1 | 6/2006 | Bess et al. | |
| 7,648,712 B2 | 1/2010 | Bess et al. | |
| 7,858,110 B2 | 12/2010 | Kuzma et al. | |
| 2001/0006677 A1 | 7/2001 | Mcginity et al. | |
| 2002/0028857 A1 | 3/2002 | Holy | |
| 2003/0153983 A1 | 8/2003 | Miller et al. | |
| 2003/0170305 A1 | 9/2003 | O'Neil et al. | |
| 2004/0002729 A1 | 1/2004 | Zamore | |
| 2004/0175428 A1 | 9/2004 | Appel et al. | |
| 2005/0037078 A1* | 2/2005 | Kuo et al. | 424/469 |
| 2005/0202371 A1* | 9/2005 | McGuire | 433/201.1 |
| 2006/0110428 A1 | 5/2006 | deJuan et al. | |
| 2006/0204540 A1 | 9/2006 | Kuzma et al. | |
| 2006/0204559 A1 | 9/2006 | Bess et al. | |
| 2008/0004260 A1* | 1/2008 | Singh | 514/220 |
| 2009/0098182 A1 | 4/2009 | Kuzma et al. | |
| 2009/0208540 A1 | 8/2009 | Kuzma et al. | |
| 2010/0080835 A1 | 4/2010 | Kuzma et al. | |
| 2010/0203104 A1* | 8/2010 | De Graaff et al. | 424/432 |
| 2011/0059147 A1 | 3/2011 | Kuo et al. | |
| 2011/0184376 A1 | 7/2011 | Kuzma et al. | |

FOREIGN PATENT DOCUMENTS

| | | |
|---|---|---|
| CN | 1863504 A | 11/2006 |
| CN | 101193626 A | 6/2008 |
| EP | 0 200 224 | 11/1986 |
| EP | 0 241 178 A1 | 10/1987 |
| EP | 1660034 | 5/2006 |

(Continued)

OTHER PUBLICATIONS

Nyberg et al. "Suggested Minimal Effective Dose of Risperidone Based on PET-Measured D2 and 5-HT2A Receptor Occupancy in Schizophrenic Patients", Am J Psychiatry, 156(6), 1999, pp. 869-875.*
Final Office Action received for U.S. Appl. No. 10/915,625 dated Mar. 16, 2009.
Final Office Action received for U.S. Appl. No. 10/915,625 dated Mar. 31, 2010.
First Examination Report issued for Indian Appln. No. 282/MUMNP/2006 received Aug. 4, 2008. (Translation only).
First Office Action received for Chinese Appln. No. 200480029342.0 dated Sep. 21, 2007, Not in English.
First Official Action received for Mexican Appln. No. PA/a/2006-001612 dated Jul. 25, 2008, Not in English.
Fourth Official Action received for Mexican Appln. No. PA/a/2006-001612 dated Jan. 18, 2010.

(Continued)

*Primary Examiner* — Kortney L Klinkel
*Assistant Examiner* — Melissa Javier
(74) *Attorney, Agent, or Firm* — RatnerPrestia

(57) ABSTRACT

This invention is related to the use of polyurethane-based polymer as a drug delivery device to deliver biologically active risperidone at a constant rate for an extended period of time and methods of manufactures thereof. The device is very biocompatible and biostable, and is useful as an implant in patients (humans and animals) for the delivery of risperidone to tissues or organs.

38 Claims, 13 Drawing Sheets

(56) References Cited

FOREIGN PATENT DOCUMENTS

| EP | 1 982 695 | | 10/2008 |
|---|---|---|---|
| JP | 10-076016 | | 3/1998 |
| JP | 2007-502139 | A | 2/2007 |
| JP | 2010-511713 | | 4/2010 |
| WO | WO-01/43726 | | 6/2001 |
| WO | WO 01/70194 | A1 | 9/2001 |
| WO | WO-2005/013936 | | 2/2005 |
| WO | WO-2006/078320 | | 7/2006 |
| WO | WO-2006/099288 | | 9/2006 |
| WO | WO 2008/070118 | | 6/2008 |
| WO | WO2008/070118 | * | 6/2008 |
| WO | WO-2009/158415 | A1 | 12/2009 |
| WO | WO-2010/039641 | A2 | 4/2010 |
| WO | WO-2010/039717 | A1 | 4/2010 |
| WO | WO-2010/039722 | A1 | 4/2010 |

OTHER PUBLICATIONS

Grigorieva, M. et al., "Polyurethane composites for medical applications," Advances in Plastics Technology, International Conference, 5th, Katowice, Poland Nov. 4-6 2003, 1 page. (Abstract only).
Hsu et al., "Plasma-induced Graft Polymerization of L-Lactide on Polyurethane," 24th Annual Mtg. Soc. Biomat., Apr. 22-26, 1998, San Diego, CA, 1 page.
International Search Report and Written Opinion for PCT/US2009/058578 mailed Feb. 2, 2010.
International Search Report and Written Opinion for PCT/US2009/058801 dated Feb. 5, 2010.
International Search Report and Written Opinion for PCT/US2009/059012 mailed Dec. 17, 2009.
International Search Report and Written Opinion received for PCT/US2009/058810 dated Feb. 3, 2010.
Non-final Office Action on U.S. Appl. No. 10/915,625 dated Sep. 29, 2009.
Non-final Office Action received for U.S. Appl. No. 10/915,625 dated Sep. 7, 2007.
Non-final Office Action received on U.S. Appl. No. 12/242,497 dated Feb. 3, 2010.
Radebough, et al., "Remington: The Science and Practice of Pharmacy, Remington's Pharmaceutical Sciences," 19th ed., Mack Publishing Co., Easton, PA, vol. 2, p. 1447-1462, (1995).
Second Office Action received for Chinese Appln. No. 200480029342,0 dated Nov. 27, 2009, Not in English.
Second Official Action received for Mexican Appln. No. PA/a/2006-001612 dated Jan. 20, 2009, Not in English.
Third Official Action received for Mexican Appln. No. PA/a/2006-001612 dated Jul. 22, 2009.
Ulrich, H., "PolyUrethanes, Encyclopedia of Polymer Science and Technology," John Wiley & Sons, 2002, accessed Aug. 31, 2007 at http://www.wiley.com, 3 pages.
Zondervan et al., "Design of a polyurethane membrane for the encapsulation of islets of Langerhans," 1992, Biomaterials 13(3):136-144.
Non-final Office Action received in U.S. Appl. No. 12/351,617 mailed Dec. 8, 2010.
International Search Report and Written Opinion received for PCT/US2009/058571 dated May 31, 2010.
Notice of Allowance received for U.S. Appl. No. 10/915,625 dated Jul. 6, 2010.
Notice of Allowance received for U.S. Appl. No. 12/242,497 dated Sep. 16, 2010.
Non-final Office Action received for U.S. Appl. No. 12/873,130 dated Oct. 4, 2011.
Non-final Office Action received for U.S. Appl. No. 12/907,717 dated Feb. 27, 2012.
Notice of Allowance received for U.S. Appl. No. 12/873,130 dated Feb. 27, 2012.
Israel Ministry of Justice Patent Office, Notification of Defects in Patent Application No. 211954, dated Dec. 22, 2013.
U.S. Appl. No. 13/121,152, Non Final Office Action mailed Dec. 27, 2012, 18 pgs.
Japanese Office Action mailed Nov. 12, 2013 for corresponding Japanese Application No. JP 2011-529355, including English language translation.
Mexican Office Action mailed Oct. 7, 2013 for corresponding Mexican Application No. MX/a/2012/006029.
Japanese Office Action mailed Nov. 12, 2013 for corresponding Japanese Application No. JP 2011-529360, including English language translation.
European Summons to attend oral proceedings pursuant to Rule 115(1) EPC mailed Oct. 21, 2013 for corresponding European Patent Application No. 08010973.9.
Chinese Office Action mailed Oct. 21, 2013 for corresponding Chinese Patent Application No. 200980142114.7, including English language translation.
Translation of Ukraine Office Action mailed Dec. 3, 2013 for corresponding Ukrainian Application No. a201105432.
Russian Official Action for Application No. 2011117327, dated Sep. 18, 2013.
J. Siepmann, F. Siepmann, Mathematical modeling of drug delivery, International Journal of Pharmaceutics, 364 (2008), pp. 328-343.
Notification of First Office Action for Chinese Patent Application No. 2009 80142114.7 dated Apr. 16, 2012 (w/English language translation).
Notice of Reason for Refusal dated Oct. 11, 2011 from Japanese Application No. 2011-031294.
European Examination Report for Patent Application No. 09 737 241.1 Dated Feb. 2, 2012.
European Examination Report for Patent Application No. 09 737 493.8 Dated May 8, 2012.
Final Office Action for Japanese Patent Application No. 2011-031294 Dated May 23, 2012 (w/English Language Translation).
Notification of First Office Action for Chinese Patent Application No. 200980142350.9 Dated May 8, 2012 (w/English Language Translation).
Notice of Allowance for U.S. Appl. No. 12/873,130 Dated Sep. 25, 2012.
Notice of Allowance for U.S. Appl. No. 12/907,717 Dated Aug. 29, 2012.
Non-Final Office Action for U.S. Appl. No. 13/416,999 Dated Sep. 14, 2012.
Second Office Action for Chinese Application No. 200980142114.7 dated Feb. 28, 2013, with English language translation.
Office Action issued by the Ukraine Patent Office for Application No. a201105431 dated Mar. 21, 2013, with English language translation.
Notice of Allowance for U.S. Appl. No. 13/693,659 Dated Apr. 30, 2013.
The State Intellectual Property Office of the People's Republic of China Office Action for Application No. 200980142113.2 dated Jul. 17, 2013 (with English translation).
Ukrainian Official Action for Application No. a201105430 dated Apr. 12, 2013 (with English translation).
US Office Action for U.S. Appl. No. 13/121,152 mailed Oct. 9, 2013.
US Notice of Allowance for U.S. Appl. No. 13/952,327 mailed Oct. 11, 2013.
Japanese Office Action Issued for U.S. Appl. No. 2011-529306 Dated Apr. 1, 2014.
Office Action Issued for Japanese Application No. 2011-031294 Dated May 28, 2013.
State of Israel Registrar of Patents, Notification of Defects in Patent Application No. 211593, dated May 26, 2013.
English Translation of the Office Action Issued for Israeli Patent Application No. 211952 on Dec. 18, 2013.
Japanese Office Action Issued for Application No. 2011-529306 Dated Dec. 3, 2013.
Office Action issued by the Patent Office of the Russian Federation for Application No. 2011117328 dated Apr. 15, 2013.
Mexican Office Action dated Nov. 11, 2014 for Mexican Application Serial No. MX/a/2011/003300.
Mexican Office Action dated Nov. 10, 2014 for Mexican Application Serial No. MX/a/2011/003301.
European Extended Search Report for Application No. 14172031.8-1455 dated Oct. 27, 2014.

(56) References Cited

OTHER PUBLICATIONS

Decision of Rejection Issued by Japanese Patent Office for Application No. 2011-529360 Dated Jul. 30, 2014 (with English language translation).
Office Action Issued by the State of Israel Ministry of Justice Registrar of Patents for Application No. 211953 Dated Jul. 23, 2014.
U.S. Appl. No. 12/907,717, Notice of Allowance mailed Jun. 8, 2012.
U.S. Appl. No. 13/693,659, Notice of Allowance mailed Apr. 30, 2013.
U.S. Appl. No. 13/952,327, Notice of Allowance mailed Oct. 11, 2013.
European Application Serial No. 08010973, European Search Report dated Apr. 27, 2010.
Indian Application Serial No. 282/MUMNP/2006, First Examination Report received Aug. 4, 2008.
Office Action dated Aug. 9, 2013 for CA counterpart Appl. No. 2,437,639.
Office Action dated Jul. 3, 2013 for CN counterpart Appl. No. 2011110053656.6.
Office Action Issued by the U.S. Patent and Trademark Office for U.S. Appl. No. 12/569,558 on May 21, 2014.
U.S. Appl. No. 10/915,625, Non Final Office Action mailed Sep. 29, 2009.
U.S. Appl. No. 13/416,999, Notice of Allowance mailed Feb. 14, 2013.
U.S. Appl. No. 13/892,946 Notice of Allowance mailed Mar. 11, 2014.
Japanese Application Serial No. 2011-529355, Office Action dated Nov. 12, 2013.
Australian Patent Examination Report for Patent Application No. 2009298637 dated Sep. 23, 2014.
Chinese Decision on Rejection for Patent Application No. 200980142114.7 dated Jul. 7, 2014, with English language translation.
Chinese Fourth Office Action for Application No. 200980142350.9, dated Jul. 10, 2014, with English language translation.
Mexican Substantive Examination Report for Patent Application No. MX/a/2011/003299 dated Sep. 4, 2014, with English language translation.
Australian Patent Examination Report for Patent Application No. 2009298711 dated Sep. 12, 2014.
Office Action issued by the European Patent Office for Application No. 09 737 240.3-1460, mailed Sep. 15, 2014.
Japanese Office Action mailed Feb. 25, 2014 for Japanese Application No. JP 2012-219869, including English translation.
Office Action Issued in Japanese Patent Application No. 2011-529306 Dated Aug. 21, 2014 (with English Language Translation).
Notification of Reexamination Issued by the Chinese Patent Office for Application No. 200980142113.2 (with English translation) Dated Jul. 7, 2014.

\* cited by examiner

IMPLANTABLE DEVICE FOR THE DELIVERY OF RISPERIDONE AND METHODS OF USE THEREOF

CROSS REFERENCE TO RELATED APPLICATIONS

This application claims priority to U.S. Provisional Application No. 61/101,548 filed Sep. 30, 2008, and U.S. Provisional Application No. 61/117,448 filed Nov. 24, 2008, the entire disclosures of which are incorporated herein by reference.

BACKGROUND

Due to its excellent biocompatibility, biostability and physical properties, polyurethane or polyurethane-containing polymers have been used to fabricate a large number of implantable devices, including pacemaker leads, artificial hearts, heart valves, stent coverings, artificial tendons, arteries and veins. Formulations for delivery of active agents using polyurethane implantable devices, however, require a liquid medium or carrier for the diffusion of the drug at a zero order rate.

SUMMARY

Described herein are methods and compositions based on the unexpected discovery that solid formulations comprising one or more active agents can be used at the core of a polyurethane implantable device such that the active agent is released in a controlled-release, zero-order manner from the implantable device. The active agents and polyurethane coating can be selected based on various physical parameters, and then the release rate of the active from the implantable device can be optimized to a clinically relevant release rate based on clinical and/or in vitro trials.

One embodiment is directed to a method for delivering a formulation comprising an effective amount of risperidone to a subject, comprising: implanting an implantable device into the subject, wherein the implantable device comprises risperidone or a formulation thereof substantially surrounded by a polyurethane-based polymer. In a particular embodiment, the polyurethane-based polymer is formed from one or more polyols, wherein the general polyol structure is selected from the group consisting of

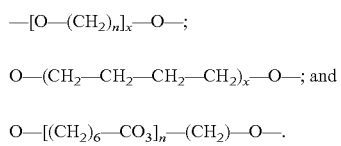

For the compositions and methods described herein, the values for n and x are integer values of between about 1 and about 1,000,000; of between about 2 and about 500,000; of between about 5 and about 250,000; and of between about 10 and about 100,000. In a particular embodiment, the polyol comprises —[O—$(CH_2)_n$]$_x$—O—, wherein the polyurethane-based polymer has an equilibrium water content of between about 5% and about 200%, e.g., of at least about 15%. In a particular embodiment, risperidone is released at a zero-order rate of about 149 μg/day per square centimeter of the surface area of the implantable device. In a particular embodiment, the polyol comprises O—$CH_2$—$CH_2$—$CH_2$—$(CH_2)_x$—O—, wherein the polyurethane-base polymer has a flex modulus of between about 1000 and about 92,000 psi, e.g., of about 2,300 psi. In a particular embodiment, risperidone is released at a zero-order rate of about 146 μg/day per square centimeter of the surface area of the implantable device. In a particular embodiment, the polyol comprises O—[$(CH_2)_6$—$CO_3$]$_n$—$(CH_2)$—O—, wherein the polyurethane-based polymer has a flex modulus of between about 620 and about 92,000 psi, e.g., of about 620 psi. In a particular embodiment, risperidone is released at a zero-order rate of about 40 μg/day per square centimeter of the surface area of the implantable device.

One embodiment is directed to a drug delivery device for the controlled release of risperidone over an extended period of time to produce local or systemic pharmacological effects, comprising: a) a polyurethane-based polymer formed to define a hollow space; and b) a solid drug formulation comprising a formulation comprising risperidone and optionally one or more pharmaceutically acceptable carriers, wherein the solid drug formulation is contained in the hollow space, and wherein the device provides a desired release rate of risperidone from the device after implantation. In a particular embodiment, the drug delivery device is conditioned and primed under conditions chosen to be consistent with the water solubility characteristics of the at least one active agent. In a particular embodiment, the pharmaceutically acceptable carrier is stearic acid. In a particular embodiment, the polyurethane-based polymer is formed from one or more polyols, wherein the general polyol structure is selected from the group consisting of:

—[O—$(CH_2)_n$]$_x$—O—;

O—$CH_2$—$CH_2$—$CH_2$—$(CH_2)_x$—O—; and

O—[$(CH_2)_6$—$CO_3$]$_n$—$(CH_2)$—O—.

In a particular embodiment, the polyol comprises —[O—$(CH_2)_n$]$_x$—O—, wherein the polyurethane-based polymer has an equilibrium water content of between about 5% and about 43%, e.g., of at least about 15%. In a particular embodiment, risperidone is released at a zero-order rate of about 149 μg/day per square centimeter of the surface area of the implantable device. In a particular embodiment, the polyol comprises O—$(CH_2$—$CH_2$—$CH_2$—$CH_2)_x$—O—, wherein the polyurethane-base polymer has a flex modulus of between about 1000 and about 92,000 psi, e.g., of about 2,300 psi. In a particular embodiment, risperidone is released at a zero-order rate of about 146 μg/day per square centimeter of the surface area of the implantable device. In a particular embodiment, the polyol comprises O—[$(CH_2)_6$—$CO_3$]$_n$—$(CH_2)$—O—, wherein the polyurethane-based polymer has a flex modulus of between about 620 and about 92,000 psi, e.g., of about 620 psi. In a particular embodiment, risperidone is released at a zero-order rate of about 40 μg/day per square centimeter of the surface area of the implantable device. In a particular embodiment, appropriate conditioning and priming parameters can be selected to establish the desired delivery rates of the at least one active agent, wherein the priming parameters are time, temperature, conditioning medium and priming medium.

BRIEF DESCRIPTION OF THE DRAWINGS

FIG. 11B is a graph of the release rate of risperidone from Tecophilic® HP-60D-20 polyurethane implants (EWC, 14.9%) alone, sampled weekly for 15 weeks.

DETAILED DESCRIPTION

Figure 1:
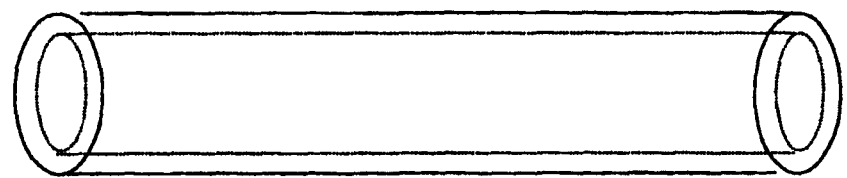
FIG. 1 is a side view of an implant with two open ends.

To take the advantage of the excellent properties of polyurethane-based polymers, the present invention is directed to the use of polyurethane-based polymers as drug delivery devices for releasing drugs at controlled rates for an extended period of time to produce local or systemic pharmacological effects. The drug delivery device can comprise a cylindrically shaped reservoir surrounded by polyurethane-based polymer that controls the delivery rate of the drug inside the reservoir. The reservoir contains a formulation, e.g., a solid formulation, comprising one or more active ingredients and, optionally, pharmaceutically acceptable carriers. The carriers are formulated to facilitate the diffusion of the active ingredients through the polymer and to ensure the stability of the drugs inside the reservoir.

A polyurethane is any polymer consisting of a chain of organic units joined by urethane links. Polyurethane polymers are formed by reacting a monomer containing at least two isocyanate functional groups with another monomer containing at least two alcohol groups in the presence of a catalyst. Polyurethane formulations cover a wide range of stiffness, hardness, and densities.

generalized polyurethane reaction

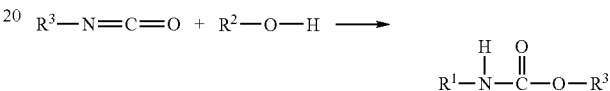

Polyurethanes are in the class of compounds called "reaction polymers," which include epoxies, unsaturated polyesters and phenolics. A urethane linkage is produced by reacting an isocyanate group, —N=C=O with a hydroxyl (alcohol) group, —OH. Polyurethanes are produced by the polyaddition reaction of a polyisocyanate with a polyalcohol (polyol) in the presence of a catalyst and other additives. In this case, a polyisocyanate is a molecule with two or more isocyanate functional groups, R—(N=C=O)$_{n≥2}$ and a polyol is a molecule with two or more hydroxyl functional groups, R'—(OH)$_{n≥2}$. The reaction product is a polymer containing the urethane linkage, —RNHCOOR'—. Isocyanates react with any molecule that contains an active hydrogen. Importantly, isocyanates react with water to form a urea linkage and carbon dioxide gas; they also react with polyetheramines to form polyureas.

Polyurethanes are produced commercially by reacting a liquid isocyanate with a liquid blend of polyols, catalyst, and other additives. These two components are referred to as a polyurethane system, or simply a system. The isocyanate is commonly referred to in North America as the "A-side" or just the "iso," and represents the rigid backbone (or "hard segment") of the system. The blend of polyols and other additives is commonly referred to as the "B-side" or as the "poly," and represents the functional section (or "soft segment") of the system. This mixture might also be called a "resin" or "resin blend." Resin blend additives can include chain extenders, cross linkers, surfactants, flame retardants, blowing agents, pigments and fillers. In drug delivery applications, the "soft segments" represent the section of the polymer that imparts the characteristics that determine the diffusivity of an active pharmaceutical ingredient (API) through that polymer.

The elastomeric properties of these materials are derived from the phase separation of the hard and soft copolymer segments of the polymer, such that the urethane hard segment domains serve as cross-links between the amorphous polyether (or polyester) soft segment domains. This phase separation occurs because the mainly non-polar, low-melting soft segments are incompatible with the polar, high-melting hard segments. The soft segments, which are formed from high molecular weight polyols, are mobile and are normally present in coiled formation, while the hard segments, which are formed from the isocyanate and chain extenders, are stiff and immobile. Because the hard segments are covalently coupled to the soft segments, they inhibit plastic flow of the polymer chains, thus creating elastomeric resiliency. Upon mechanical deformation, a portion of the soft segments are stressed by uncoiling, and the hard segments become aligned in the stress direction. This reorientation of the hard segments and consequent powerful hydrogen-bonding contributes to high tensile strength, elongation, and tear resistance values.

The polymerization reaction is catalyzed by tertiary amines, such as, for example, dimethylcyclohexylamine, and organometallic compounds, such as, for example, dibutyltin dilaurate or bismuth octanoate. Furthermore, catalysts can be chosen based on whether they favor the urethane (gel) reaction, such as, for example, 1,4-diazabicyclo[2.2.2]octane (also called DABCO or TEDA), or the urea (blow) reaction, such as bis-(2-dimethylaminoethyl)ether, or specifically drive the isocyanate trimerization reaction, such as potassium octoate.

Polyurethane polymer formed by reacting a diisocyanate with a polyol

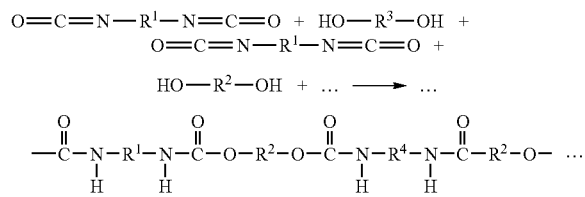

Isocyanates with two or more functional groups are required for the formation of polyurethane polymers. Volume wise, aromatic isocyanates account for the vast majority of global diisocyanate production. Aliphatic and cycloaliphatic isocyanates are also important building blocks for polyurethane materials, but in much smaller volumes. There are a number of reasons for this. First, the aromatically-linked isocyanate group is much more reactive than the aliphatic one. Second, aromatic isocyanates are more economical to use. Aliphatic isocyanates are used only if special properties are required for the final product. Light stable coatings and elastomers, for example, can only be obtained with aliphatic isocyanates. Aliphatic isocyanates also are favored in the production of polyurethane biomaterials due to their inherent stability and elastic properties.

Examples of aliphatic and cycloaliphatic isocyanates include, for example, 1,6-hexamethylene diisocyanate (HDI), 1-isocyanato-3-isocyanatomethyl-3,5,5-trimethyl-cyclohexane (isophorone diisocyanate, IPDI), and 4,4'-diisocyanato dicyclohexylmethane (H12MDI). They are used to produce light stable, non-yellowing polyurethane coatings and elastomers. H12MDI prepolymers are used to produce high performance coatings and elastomers with optical clarity and hydrolysis resistance. Tecoflex®, Tecophilic® and Carbothane® polyurethanes are all produced from H12MDI prepolymers.

Polyols are higher molecular weight materials manufactured from an initiator and monomeric building blocks, and, where incorporated into polyurethane systems, represent the "soft segments" of the polymer. They are most easily classified as polyether polyols, which are made by the reaction of epoxides (oxiranes) with an active hydrogen containing starter compounds, or polyester polyols, which are made by the polycondensation of multifunctional carboxylic acids and hydroxyl compounds.

Tecoflex® polyurethanes, Tecogel® polyurethanes and Tecophilic® polyurethanes are cycloaliphatic polymers and are of the types produced from polyether-based polyols. For the Tecoflex® polyurethanes, the general structure of the polyol segment is represented as, $$O-(CH_2-CH_2-CH_2-CH_2)_x-O-$$

whereby an increase in "x" represents a increase in flexibility (decreased "Flex Modulus"; "FM"), yielding FM ranging from about 1000-92,000 psi. From the standpoint of drug release from these materials, the release of a relatively hydrophobic API decreases as the FM increases. For the compositions and methods described herein, the values for x are integer values of between about 1 and about 1,000,000; of between about 2 and about 500,000; of between about 5 and about 250,000; and of between about 10 and about 100,000. In still other embodiments, x may range from about 2-500, about 2-100, about 5-50, and 10-30.

For the Tecophilic® (hydrophilic) or Tecogel® polyurethanes, the general structure of the polyol segment is represented as, $$-[O-(CH_2)_n]_x-O-$$

whereby increases in "n" and "x" represent variations in hydrophilicity, and yield equilibrium water contents (% EWC) ranging from about 5%-200%. For the compositions and methods described herein, the values for n and x are integer values of between about 1 and about 1,000,000; of between about 2 and about 500,000; of between about 5 and about 250,000; and of between about 10 and about 100,000. In still other embodiments, n and x may have the same or different values, with those values ranging from about 2-500, about 2-100, about 5-50, and 10-30. From the standpoint of drug release from these materials, the release of a relatively hydrophilic API increases as the % EWC increases.

Specialty polyols include, for example, polycarbonate polyols, polycaprolactone polyols, polybutadiene polyols, and polysulfide polyols.

Carbothane® polyurethanes are cycloaliphatic polymers and are of the types produced from polycarbonate-based polyols. The general structure of the polyol segment is represented as, $$O-[(CH_2)_6-CO_3]_n-(CH_2)-O-$$

whereby an increase in "n" represents a increase in flexibility (decreased FM), yielding FM ranging from about 620-92,000 psi. For the compositions and methods described herein, the values for n are integer values of between about 1 and about 1,000,000; of between about 2 and about 500,000; of between about 5 and about 250,000; and of between about 10 and about 100,000. In still other embodiments, n may range from about 2-500, about 2-100, about 5-50, and 10-30. From the standpoint of drug release from these materials, the release of a relatively hydrophobic API will decrease as the FM increases.

Chain extenders and cross linkers are low molecular weight hydroxyl- and amine-terminated compounds that play an important role in the polymer morphology of polyurethane fibers, elastomers, adhesives and certain integral skin and microcellular foams. Examples of chain extenders include, for example, ethylene glycol, 1,4-butanediol (1,4-BDO or BDO), 1,6-hexanediol, cyclohexane dimethanol and hydroquinone bis(2-hydroxyethyl)ether (HQEE). All of these glycols form polyurethanes that phase separate well, form well-defined hard segment domains, and are melt processable. They are all suitable for thermoplastic polyurethanes with the exception of ethylene glycol, since its derived bis-phenyl urethane undergoes unfavorable degradation at high hard segment levels. Tecophilic®, Tecoflex® and Carbothane® polyurethanes all incorporate the use of 1,4-butanediol as the chain extender.

The current invention provides a drug delivery device that can achieve the following objectives: a controlled-release rate (e.g., zero-order release rate) to maximize therapeutic effects and minimize unwanted side effects, an easy way to retrieve the device if it is necessary to end the treatment, an increase in bioavailability with less variation in absorption and no first pass metabolism.

The release rate of the drug is governed by the Fick's Law of Diffusion as applied to a cylindrically shaped reservoir device (cartridge). The following equation describes the relationship between different parameters:

$$\frac{dM}{dt} = \frac{2\pi h p \Delta C}{\ln(r_o/r_i)}$$

where:
dM/dt: drug release rate;
h: length of filled portion of device;
ΔC: concentration gradient across the reservoir wall;
$r_o/r_i$: ratio of outside to inside radii of device; and
p: permeability coefficient of the polymer used.

The permeability coefficient is primarily regulated by the hydrophilicity or hydrophobicity of the polymer, the structure of the polymer, and the interaction of drug and the polymer. Once the polymer and the active ingredient are selected, p is a constant, h, ro, and $r_i$ are fixed and kept constant once the cylindrically shaped device is produced. ΔC is maintained constant.

To keep the geometry of the device as precise as possible, the device, e.g., a cylindrically shaped device, can be manufactured through precision extrusion or precision molding process for thermoplastic polyurethane polymers, and reaction injection molding or spin casting process for thermosetting polyurethane polymers.

The cartridge can be made with either one end closed or both ends open. The open end can be plugged with, for example, pre-manufactured end plug(s) to ensure a smooth end and a solid seal, or, in the case of thermoplastic polyurethanes, by using heat-sealing techniques known to those skilled in the art. The solid actives and carriers can be compressed into pellet form to maximize the loading of the actives.

To identify the location of the implant, radiopaque material can be incorporated into the delivery device by inserting it into the reservoir or by making it into end plug to be used to seal the cartridge.

Once the cartridges are sealed on both ends with the filled reservoir, they are optionally conditioned and primed for an appropriate period of time to ensure a constant delivery rate.

The conditioning of the drug delivery devices involves the loading of the actives (drug) into the polyurethane-based polymer that surrounds the reservoir. The priming is done to stop the loading of the drug into the polyurethane-based polymer and thus prevent loss of the active before the actual use of the implant. The conditions used for the conditioning and priming step depend on the active, the temperature and the medium in which they are carried out. The conditions for the conditioning and priming may be the same in some instances.

The conditioning and priming step in the process of the preparation of the drug delivery devices is done to obtain a determined rate of release of a specific drug. The conditioning and priming step of the implant containing a hydrophilic drug can be carried out in an aqueous medium, e.g., in a saline solution. The conditioning and priming step of a drug delivery device comprising a hydrophobic drug is usually carried out in a hydrophobic medium such as, for example, an oil-based medium. The conditioning and priming steps can be carried out by controlling three specific factors, namely the temperature, the medium and the period of time.

A person skilled in the art would understand that the conditioning and priming step of the drug delivery device is affected by the medium in which the device is placed. A hydrophilic drug can be conditioned and primed, for example, in an aqueous solution, e.g., in a saline solution. The temperature used to condition and prime the drug delivery device can vary across a wide range of temperatures, e.g., about 37° C.

The time period used for the conditioning and priming of the drug delivery devices can vary from about a single day to several weeks depending on the release rate desired for the specific implant or drug. The desired release rate is determined by one of skill in the art with respect to the particular active agent used in the pellet formulation.

A person skilled in the art will understand the steps of conditioning and priming the implants are to optimize the rate of release of the drug contained within the implant. As such, a shorter time period spent on the conditioning and the priming of a drug delivery device results in a lower rate of release of the drug compared to a similar drug delivery device that has undergone a longer conditioning and priming step.

The temperature in the conditioning and priming step will also affect the rate of release in that a lower temperature results in a lower rate of release of the drug contained in the drug delivery device when compared to a similar drug delivery device that has undergone a treatment at a higher temperature.

Similarly, in the case of aqueous solutions, e.g., saline solutions, the sodium chloride content of the solution determines what type of rate of release will be obtained for the drug delivery device. More specifically, a lower content of sodium chloride results in a higher rate of release of drug when compared to a drug delivery device that has undergone a conditioning and priming step where the sodium chloride content was higher.

The same conditions apply for hydrophobic drugs where the main difference in the conditioning and priming step is that the conditioning and priming medium is a hydrophobic medium, more specifically an oil-based medium.

The delivery of risperidone can be useful, for example, to treat schizophrenia, manic states, bipolar disorder, irritability, autism, obsessive-compulsive disorder, severe treatment-resistant depression with or without psychotic features, Tourette syndrome, disruptive behavior disorders in children; and eating disorders. Risperidone belongs to a class of antipsychotic drugs known as "atypical neuroleptics". It is a strong dopamine antagonist. It has a high affinity for D2 dopaminergic receptors. It has actions at several 5-HT (serotonin) receptor subtypes. These are 5-HT2C, linked to weight gain, 5-HT2A, linked to its antipsychotic action and relief of some of the extrapyramidal side effects experienced with the "typical neuroleptics" through action at 5-HT1A. The latter action leads to an increased release of dopamine from mesocortical neurons in the brain. Effective levels of risperidone in the blood are known and established and can range, for example, about 0.1 to about 10 ng/ml, from about 0.5 to about 8 ng/ml or about 1.0 to about 5 ng/ml range.

One of skill in the art would be able to tailor risperidone release by altering a variety of implant factors. For example, as shown in the Examples, different classes of polyurethanes lead to different release rates of risperidone. Additionally, within classes of polyurethanes, the EWC and/or flex modulus of the polyurethane can be varied to achieve different risperidone release rates. Further still, one of skill in the art could vary the size of the implant to increase or decrease the surface area of the implant, thereby varying the release rate of risperidone from the implant. Such alterations lead to release rates in the physiologically-relevant range, e.g., of about 0.001 to about 15 mg/day, from about 0.1 to about 15 mg/day, from about 1 to about 12.5 mg/day, from about 7.5 to about 12.5 mg/day or at about 12.5 mg/day. Release rate from implants can also be varied, for example, by adjusting the amount and nature of excipients contained in the risperidone formulation.

Implants that achieve physiological release rates of risperidone can vary in size, depending on, for example, the nature of the polyurethane used. A cylindrical implant, for example, can have a range of internal diameters from about 1 mm to about 10 mm, from about 1.5 mm to about 5 mm, from about 1.8 mm to about 3.6 mm, about 3.6 mm or about 1.8 mm. An implant can range in length from about, for example, 5 mm to about 100 mm, from about 7.5 mm to about 50 mm, from about 10 mm to about 40 mm, from about 15 mm to about 30 mm, about 37 mm, about 40 mm or about 15.24 mm.

The current invention focuses on the application of polyurethane-based polymers, thermoplastics or thermosets, to the creation of implantable drug devices to deliver biologically active compounds at controlled rates for prolonged period of time. Polyurethane polymers can be made into, for example, cylindrical hollow tubes with one or two open ends through extrusion, (reaction) injection molding, compression molding, or spin-casting (see e.g., U.S. Pat. Nos. 5,266,325 and 5,292,515), depending on the type of polyurethane used.

Thermoplastic polyurethane can be processed through extrusion, injection molding or compression molding. Thermoset polyurethane can be processed through reaction injection molding, compression molding, or spin-casting. The dimensions of the cylindrical hollow tube should be as precise as possible.

Polyurethane-based polymers are synthesized from multifunctional polyols, isocyanates and chain extenders. The characteristics of each polyurethane can be attributed to its structure.

Thermoplastic polyurethanes are made of macrodiols, diisocyanates, and difunctional chain extenders (e.g., U.S. Pat. Nos. 4,523,005 and 5,254,662). Macrodiols make up the soft domains. Diisocyanates and chain extenders make up the hard domains. The hard domains serve as physical crosslinking sites for the polymers. Varying the ratio of these two domains can alter the physical characteristics of the polyurethanes, e.g., the flex modulus.

Thermoset polyurethanes can be made of multifunctional (greater than difunctional) polyols and/or isocyanates and/or chain extenders (e.g., U.S. Pat. Nos. 4,386,039 and 4,131,604). Thermoset polyurethanes can also be made by introducing unsaturated bonds in the polymer chains and appropriate crosslinkers and/or initiators to do the chemical crosslinking (e.g., U.S. Pat. No. 4,751,133). By controlling the amounts of crosslinking sites and how they are distributed, the release rates of the actives can be controlled.

Different functional groups can be introduced into the polyurethane polymer chains through the modification of the backbones of polyols depending on the properties desired. Where the device is used for the delivery of water soluble drugs, hydrophilic pendant groups such as ionic, carboxyl, ether, and hydroxyl groups are incorporated into the polyols to increase the hydrophilicity of the polymer (e.g., U.S. Pat. Nos. 4,743,673 and 5,354,835). Where the device is used for the delivery of hydrophobic drugs, hydrophobic pendant groups such as alkyl, siloxane groups are incorporated into the polyols to increase the hydrophobicity of the polymer (e.g., U.S. Pat. No. 6,313,254). The release rates of the actives can also be controlled by the hydrophilicity/hydrophobicity of the polyurethane polymers.

For thermoplastic polyurethanes, precision extrusion and injection molding are the preferred choices to produce two open-end hollow tubes (FIG. 1) with consistent physical dimensions. The reservoir can be loaded freely with appropriate formulations containing actives and carriers or filled with pre-fabricated pellets to maximize the loading of the actives. One open end needs to be sealed first before the loading of the formulation into the hollow tube. To seal the two open ends, two pre-fabricated end plugs (FIG. 2) can be used. The sealing step can be accomplished through the application of heat or solvent or any other means to seal the ends, preferably permanently.

For thermoset polyurethanes, precision reaction injection molding or spin casting is the preferred choice depending on the curing mechanism. Reaction injection molding is used if the curing mechanism is carried out through heat and spin casting is used if the curing mechanism is carried out through light and/or heat. Hollow tubes with one open end (FIG. 3), for example, can be made by spin casting. Hollow tubes with two open ends, for example, can be made by reaction injection molding. The reservoir can be loaded in the same way as the thermoplastic polyurethanes.

To seal an open end, an appropriate light-initiated and/or heat-initiated thermoset polyurethane formulation can be used to fill the open end, and this is cured with light and/or heat. A pre-fabricated end plug, for example, can also be used to seal the open end by applying an appropriate light-initiated and/or heat-initiated thermoset polyurethane formulation on to the interface between the pre-fabricated end plug and the open end, and curing it with the light and/or heat or any other means to seal the ends, preferably permanently.

The final process involves the conditioning and priming of the implants to achieve the delivery rates required for the actives. Depending upon the types of active ingredient, hydrophilic or hydrophobic, the appropriate conditioning and priming media is chosen. Water-based media are preferred for hydrophilic actives, and oil-based media are preferred for hydrophobic actives.

As a person skilled in the art would readily know many changes can be made to the preferred embodiments of the invention without departing from the scope thereof. It is intended that all matter contained herein be considered illustrative of the invention and not it a limiting sense.

EXEMPLIFICATION

Example 1

Figure 2:
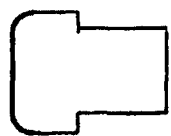
FIG. 2 is a side view of pre-fabricated end plugs used to plug the implants.
Figure 2:
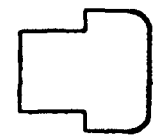
Figure 3:
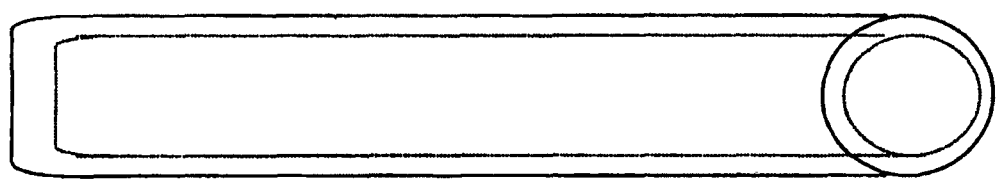
FIG. 3 is a side view of an implant with one open end.
Figure 4A:
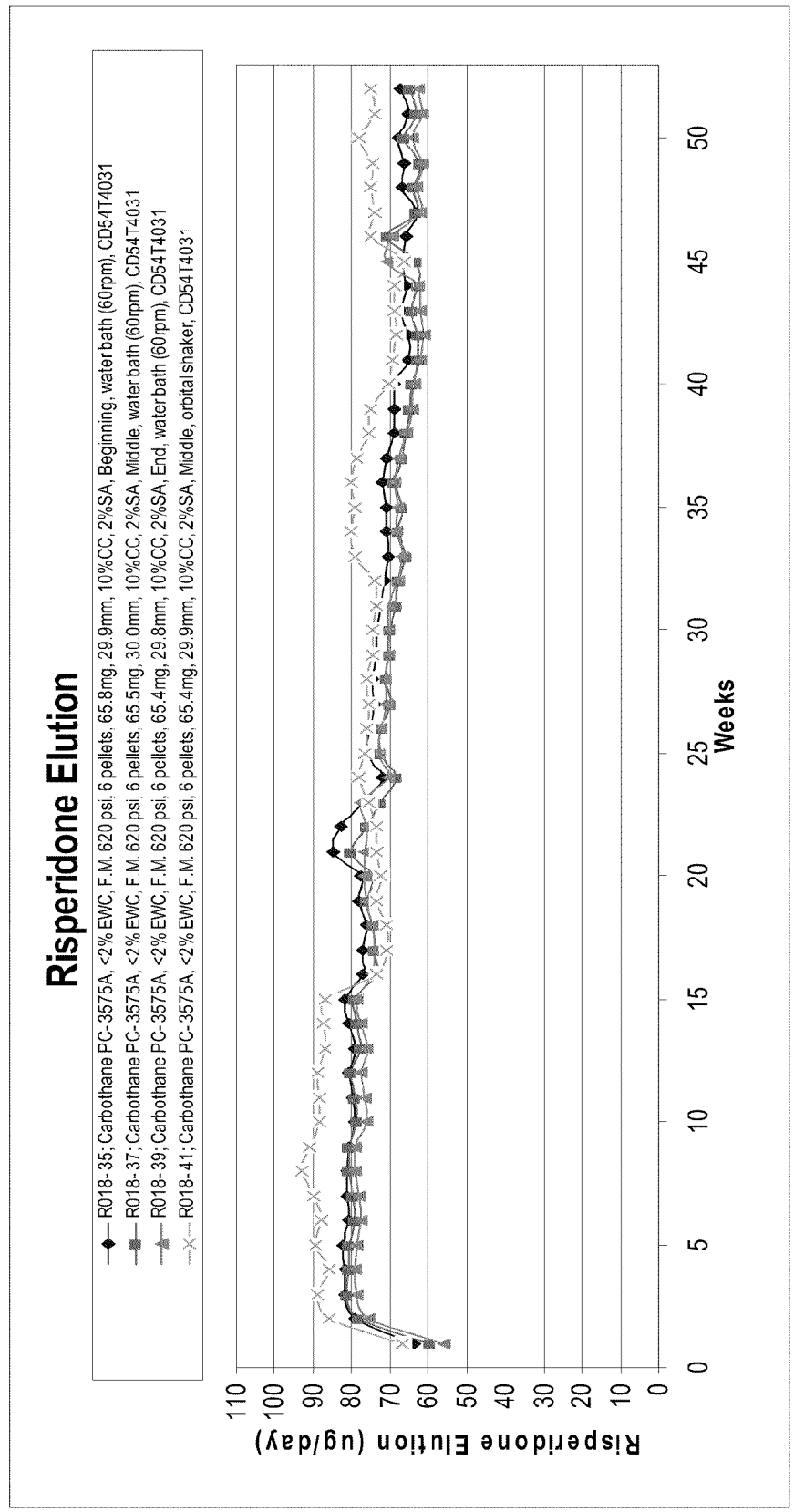
FIG. 4 is a graph of the release rate of risperidone from Carbothane® PC-3575A polyurethane implants (Flex Modulus 620 psi) prepared from tubing sections representing the beginning, middle and end of a coil of tubing as part of an assessment of the uniformity of the material within a particular lot. Samples were evaluated weekly for one year. All implants were of equivalent geometry and drug load.
Figure 4B:
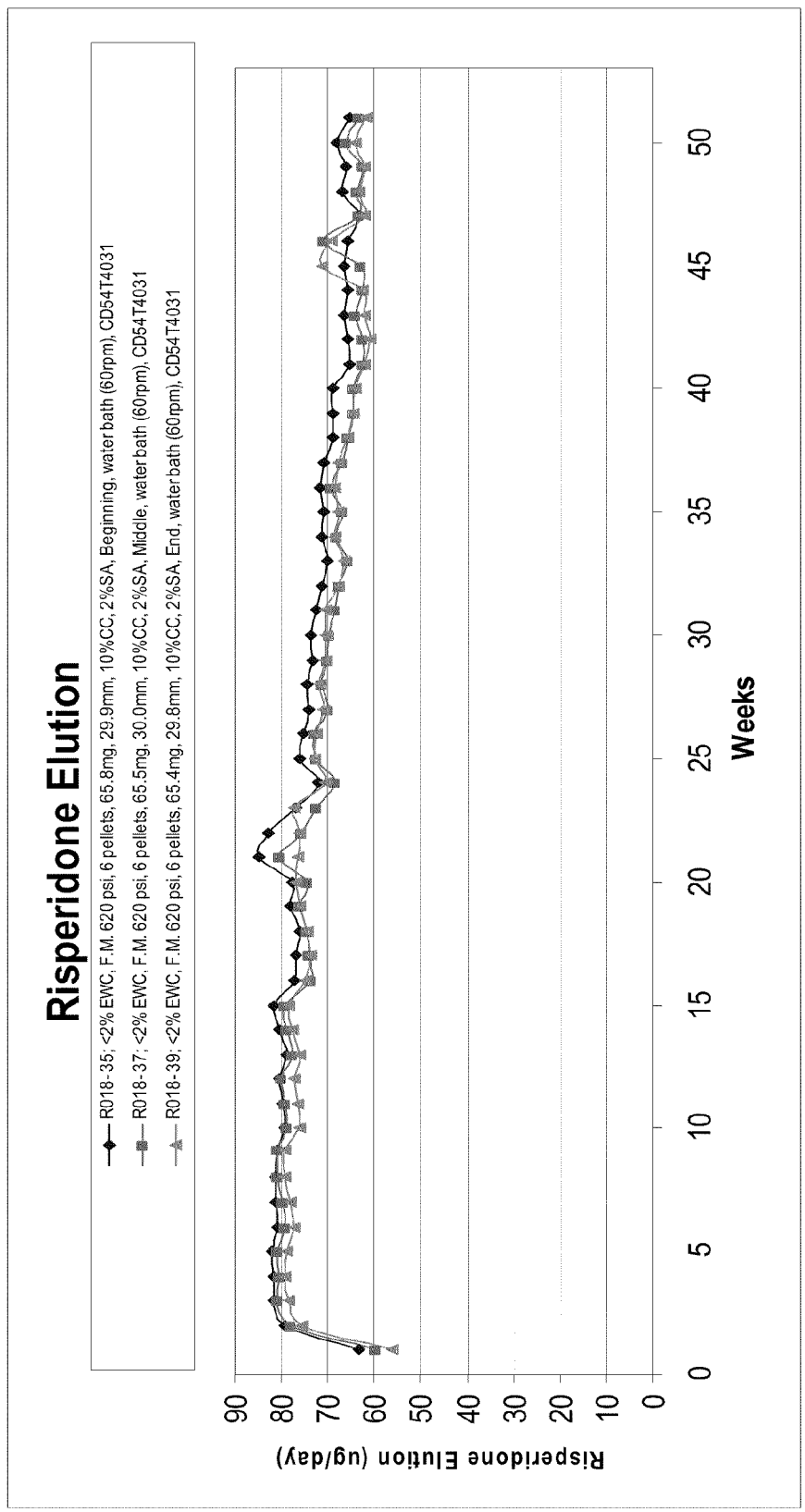

Tecophilic® polyurethane polymer tubes are supplied by Thermedics Polymer Products and manufactured through a precision extrusion process. Tecophilic® polyurethane is a family of aliphatic polyether-based thermoplastic polyurethane that can be formulated to different equilibrium water contents (EWC) of up to 150% of the weight of dry resin. Extrusion grade formulations are designed to provide maximum physical properties of thermoformed tubing or other components. An exemplary tube and end cap structures are depicted in FIGS. 1-3.

The physical data for the polymers is provided below as made available by Thermedics Polymer Product (tests conducted as outlined by American Society for Testing and Materials (ASTM), Table 1).

TABLE 1

| Tecophilic ® Typical Physical Test Data | | | | | |
|---|---|---|---|---|---|
| | ASTM | HP-60D-20 | HP-60D-35 | HP-60D-60 | HP-93A-100 |
| Durometer (Shore Hardness) | D2240 | 43D | 42D | 41D | 83A |
| Spec Gravity | D792 | 1.12 | 1.12 | 1.15 | 1.13 |
| Flex Modulus (psi) | D790 | 4,300 | 4,000 | 4,000 | 2,900 |
| Ultimate Tensile Dry (psi) | D412 | 8,900 | 7,800 | 8,300 | 2,200 |
| Ultimate Tensile Wet (psi) | D412 | 5,100 | 4,900 | 3,100 | 1,400 |
| Elongation Dry (%) | D412 | 430 | 450 | 500 | 1,040 |
| Elongation Wet (%) | D412 | 390 | 390 | 300 | 620 |

Example 2

Tables 2A-C show release rates of risperidone from three different classes of polyurethane compounds (Tecophilic®, Tecoflex® and Carbothane®). The release rates have been normalized to surface area of the implant, thereby adjusting for slight differences in the size of the various implantable devices. Risperidone is considered to be hydrophobic (not very water-soluble), as indicated by the Log P value; for the purposes of the data provided, a Log P value of greater than about 2.0 is considered to be not readily soluble in aqueous solution. The polyurethanes were selected to have varying affinities for water soluble active agents and varying flexibility (as indicated by the variation in flex modulus).

For applications of the polyurethanes useful for the devices and methods described herein, the polyurethane exhibits physical properties suitable for the risperidone formulation to be delivered. Polyurethanes are available or can be prepared, for example, with a range of EWCs or flex moduli (Table 2). Tables 2A-C show normalized release rates for various active ingredients from polyurethane compounds. Tables 2D-F show the non-normalized release rates for the same active ingredients, together with implant composition.

TABLE 2A

| | | Polyurethane Type Tecophilic Polyurethane Grade | | | | |
|---|---|---|---|---|---|---|
| Active | Relative Water Solubility | HP-60D-60 31% EWC | HP-60D-35 24% EWC | HP-60D-20 % EWC/Flex Modulus 15% EWC | HP-60D-10 8.7% EWC | HP-60D-05 5.5% EWC |
| Risperidone (M.W. 410) | Log P = 3.28 | — | — | 149 μg/day/cm² 10% CC, 2% SA, 28.5 mg API | — | — |

TABLE 2B

| | | Polyurethane Type Tecoflex Polyurethane Grade | | |
|---|---|---|---|---|
| Active | Relative Water Solubility | EG-85A F.M.: 2,300 | EG 100A % EWC/Flex Modulus F.M.: 10,000 | EG-65D F.M.: 37,000 |
| Risperidone (M.W. 410) | Log P = 3.28 | 146 μg/day/cm² 10% CC, 2% SA, 27.9 mg API | 7.6 μg/day/cm² 10% CC, 2% SA, 29.8 mg API | 1.9 μg/day/cm² 10% CC, 2% SA, 29.7 mg API |

TABLE 2C

| | | Polyurethane Type Carbothane Polyurethane Grade | |
|---|---|---|---|
| Active | Relative Water Solubility | PC-3575A % EWC/Flex Modulus F.M.: 620 | PC-3595A F.M.: 4,500 |
| Risperidone (M.W. 410) | Log P = 3.28 | 40 μg/day/cm² 10% CC, 2% SA, 27.8 mg API | 11 μg/day/cm² 10% CC, 2% SA, 29.7 mg API |

TABLE 2D

| | Relative Water Solubility | Polyurethane Tecophilic Grade | | | | |
|---|---|---|---|---|---|---|
| | | HP-60D-60 | HP-60D-35 | HP-60D-20 % EWC | HP-60D-10 | HP-60D-05 |
| Active | | 31% EWC | 24% EWC | 15% EWC | 8.7% EWC | 5.5% EWC |
| Risperidone (M.W. 410) | Log P = 3.28 | — | — | 150 µg/day ID: 1.80 mm Wall: 0.30 mm L: 15.24 mm 1.005 cm² | — | — |

TABLE 2E

| | Relative Water Solubility | Polyurethane Type Tecoflex Polyurethane Grade | | |
|---|---|---|---|---|
| | | EG-85A | EG 100A Flex Modulus | EG-65D |
| Active | | F.M.: 2,300 | F.M.: 10,000 | F.M.: 37,000 |
| Risperidone (M.W. 410) | Log P = 3.28 | 150 µg/day ID: 1.85 mm Wall: 0.20 mm L: 16.0 mm 1.030 cm² | 8 µg/day ID: 1.85 mm Wall: 0.20 mm L: 16.4 mm 1.056 cm² | 2 µg/day ID: 1.85 mm Wall: 0.20 mm L: 16.2 mm 1.043 cm² |

TABLE 2F

| | Relative Water Solubility | Polyurethane Type Carbothane Polyurethane Grade | |
|---|---|---|---|
| | | PC-3575A Flex Modulus | PC-3595A |
| Active | | F.M.: 620 | F.M.: 4,500 |
| Risperidone (M.W. 410) | Log P = 3.28 | 40 µg/day ID: 1.85 mm Wall: 0.20 mm L: 15.6 mm 1.004 cm² | 11 µg/day ID: 1.85 mm Wall: 0.20 mm L: 16.2 mm 1.043 cm² |

The solubility of an active agent in an aqueous environment can be measured and predicted based on its partition coefficient (defined as the ratio of concentration of compound in aqueous phase to the concentration in an immiscible solvent). The partition coefficient (P) is a measure of how well a substance partitions between a lipid (oil) and water. The measure of solubility based on P is often given as Log P. In general, solubility is determined by Log P and melting point (which is affected by the size and structure of the compounds). Typically, the lower the Log P value, the more soluble the compound is in water. It is possible, however, to have compounds with high Log P values that are still soluble on account of, for example, their low melting point. It is similarly possible to have a low Log P compound with a high melting point, which is very insoluble.

The flex modulus for a given polyurethane is the ratio of stress to strain. It is a measure of the "stiffness" of a compound. This stiffness is typically expressed in Pascals (Pa) or as pounds per square inch (psi).

The elution rate of an active agent from a polyurethane compound can vary on a variety of factors including, for example, the relative hydrophobicity/hydrophilicity of the polyurethane (as indicated, for example, by logP), the relative "stiffness" of the polyurethane (as indicated, for example, by the flex modulus), and/or the molecular weight of the active agent to be released.

Example 3

Elution of Risperidone from Polyurethane Implantable Devices

FIGS. 5-10 are graphs showing elution profiles of risperidone from various implantable devices over varying periods of time.

Figure 5:
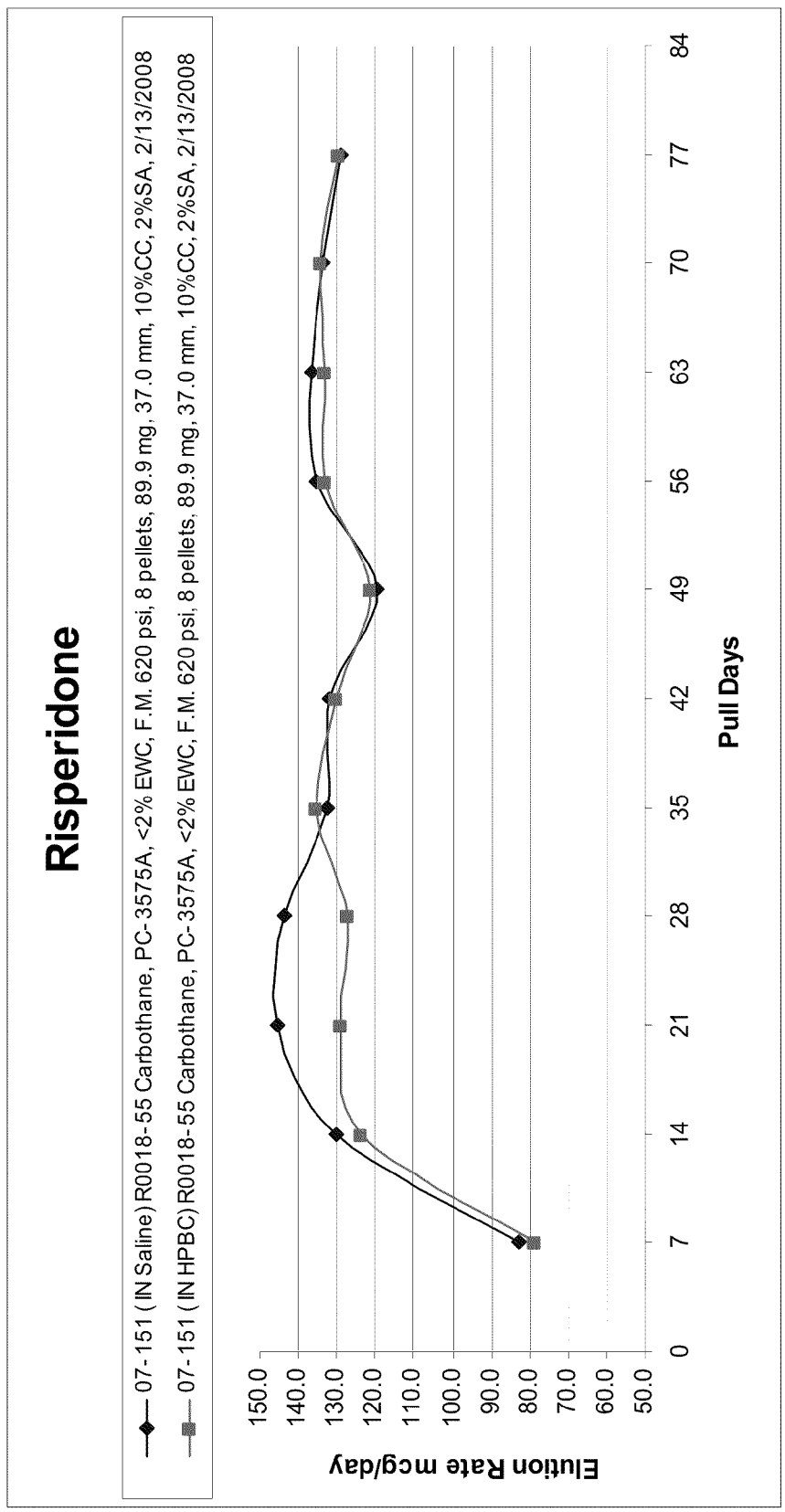
FIG. 5 is a graph of the release rate of risperidone from Carbothane® PC-3575A polyurethane implants (Flex Modulus 620 psi) as part of an assessment of the effect using saline versus aqueous hydroxypropyl betacellulose solution (15% in phosphate buffered saline) as the elution media. Samples were evaluated weekly for 11 weeks. All implants were of equivalent geometry and drug load.

Release rates were obtained for risperidone from Carbothane® PC-3575A polyurethane implants (F.M. 620 psi) prepared from tubing sections representing the beginning, middle and end of a coil of tubing as part of an assessment of the uniformity of the material within a particular lot (FIG. 5). Samples were evaluated weekly for one year. All implants were of equivalent geometry and drug load.

Figure 6A:
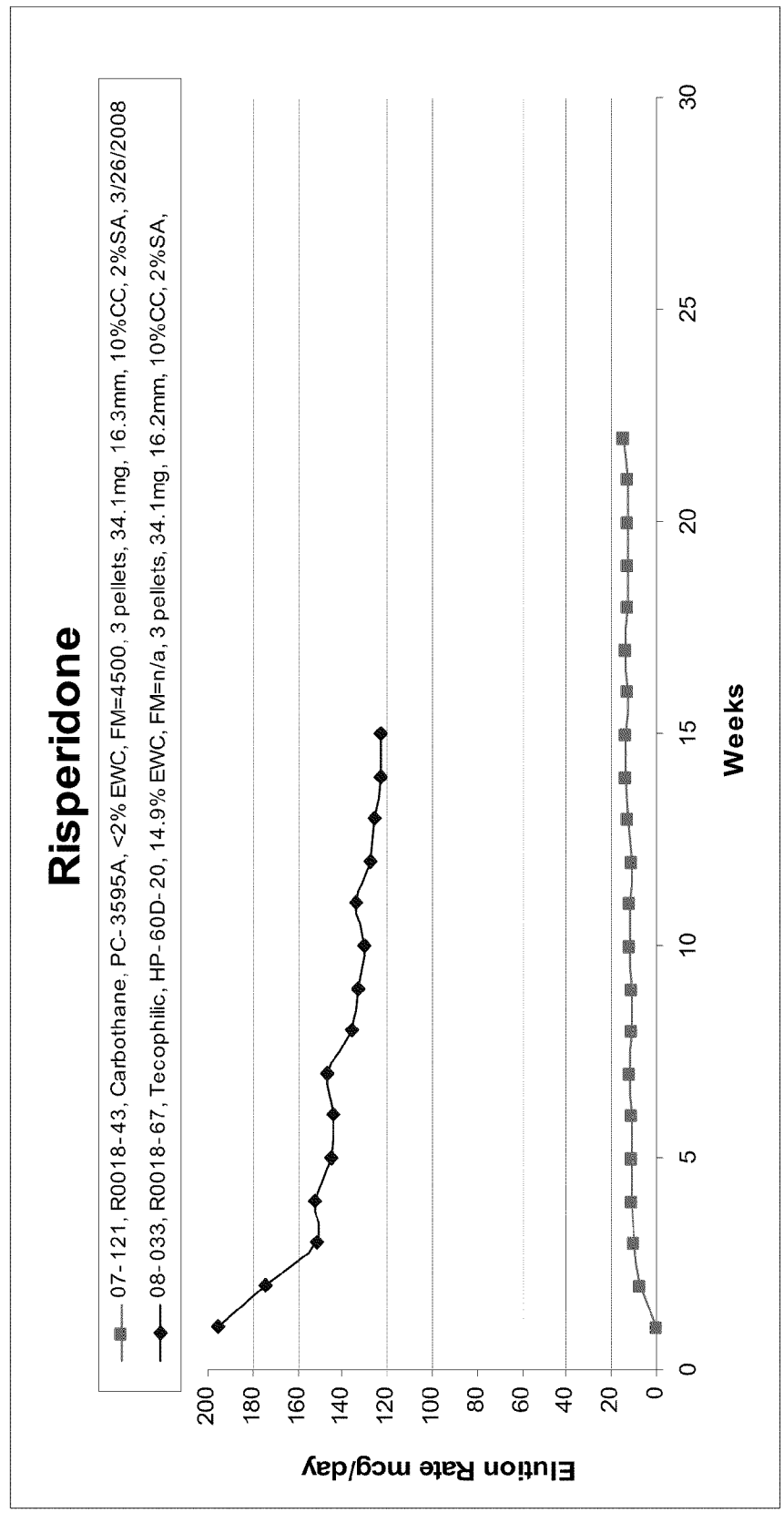
FIGS. 6A and 6B are graphs comparing the release rates of risperidone from Carbothane® PC-3595A polyurethane implants (Flex modulus 4500 psi) to Tecophilic® HP-60D-20 polyurethane implants (EWC, 14.9%) as part of the evaluation of the release of the active from either hydrophilic and hydrophobic polyurethane materials. Samples were evaluated weekly for 22 weeks for the Carbothane® implant. Samples were evaluated weekly for 15 weeks for the Tecophilic® implant. All implants were of equivalent geometry and drug load.
Figure 6B:
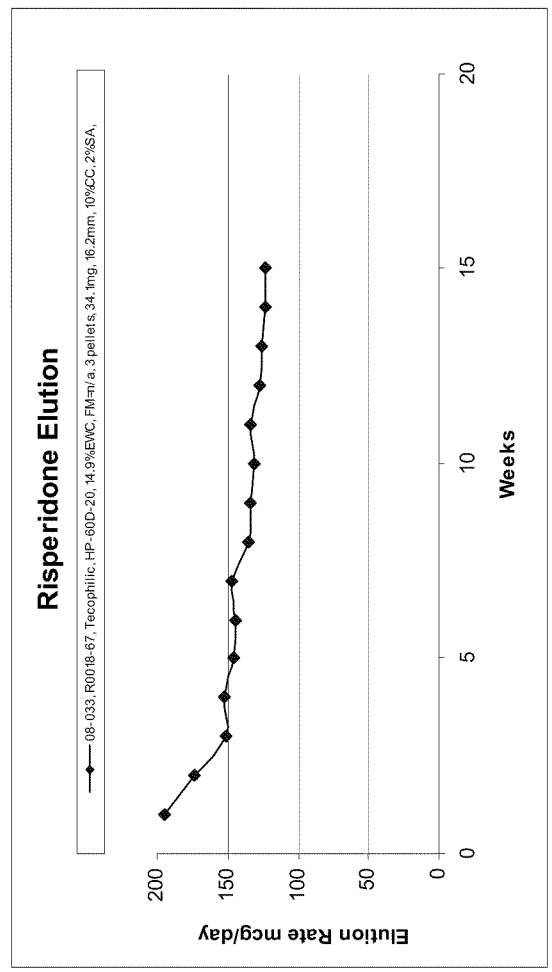
Figure 7:
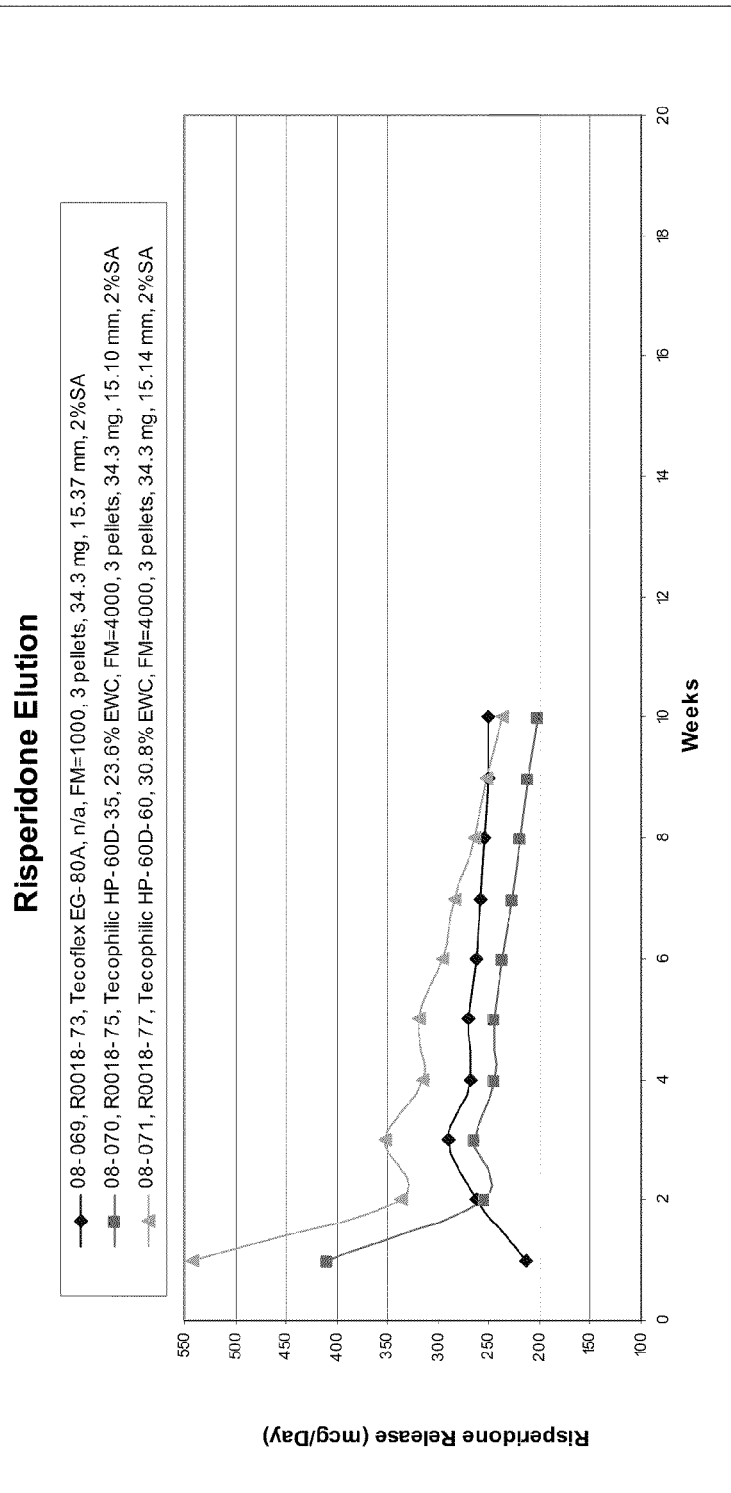
FIG. 7 is a graph comparing the release rates of risperidone from Tecoflex® EG-80A polyurethane implants (Flex Modulus 1000 psi) and two grades of Tecophilic® polyurethane implants, HP-60D-35 and HP-60D-60 (EWC, 23.6% and 30.8%, respectively). All were sampled weekly for 10 weeks. All implants were of equivalent geometry and drug load.

Release rates were obtained for risperidone from Carbothane® PC-3575A polyurethane implants (F.M. 620 psi) as part of an assessment of the effect using saline versus aqueous hydroxypropyl betacellulose solution (15% in phosphate buffered saline) as the elution media (FIG. 6). Samples were evaluated weekly for 11 weeks. All implants were of equivalent geometry and drug load.

Release rates were compared for risperidone from Carbothane® PC-3595A polyurethane implants (F.M. 4500 psi) and Tecophilic® HP-60D-20 polyurethane implants (EWC 14.9%) as part of the evaluation of the release of the active from either hydrophilic and hydrophobic polyurethane materials (FIGS. 7A and 7B). Samples were evaluated weekly for 22 weeks for the Carbothane® implant. Samples were evaluated weekly for 15 weeks for the Tecophilic® implant. All implants were of equivalent geometry and drug load.

Figure 8:
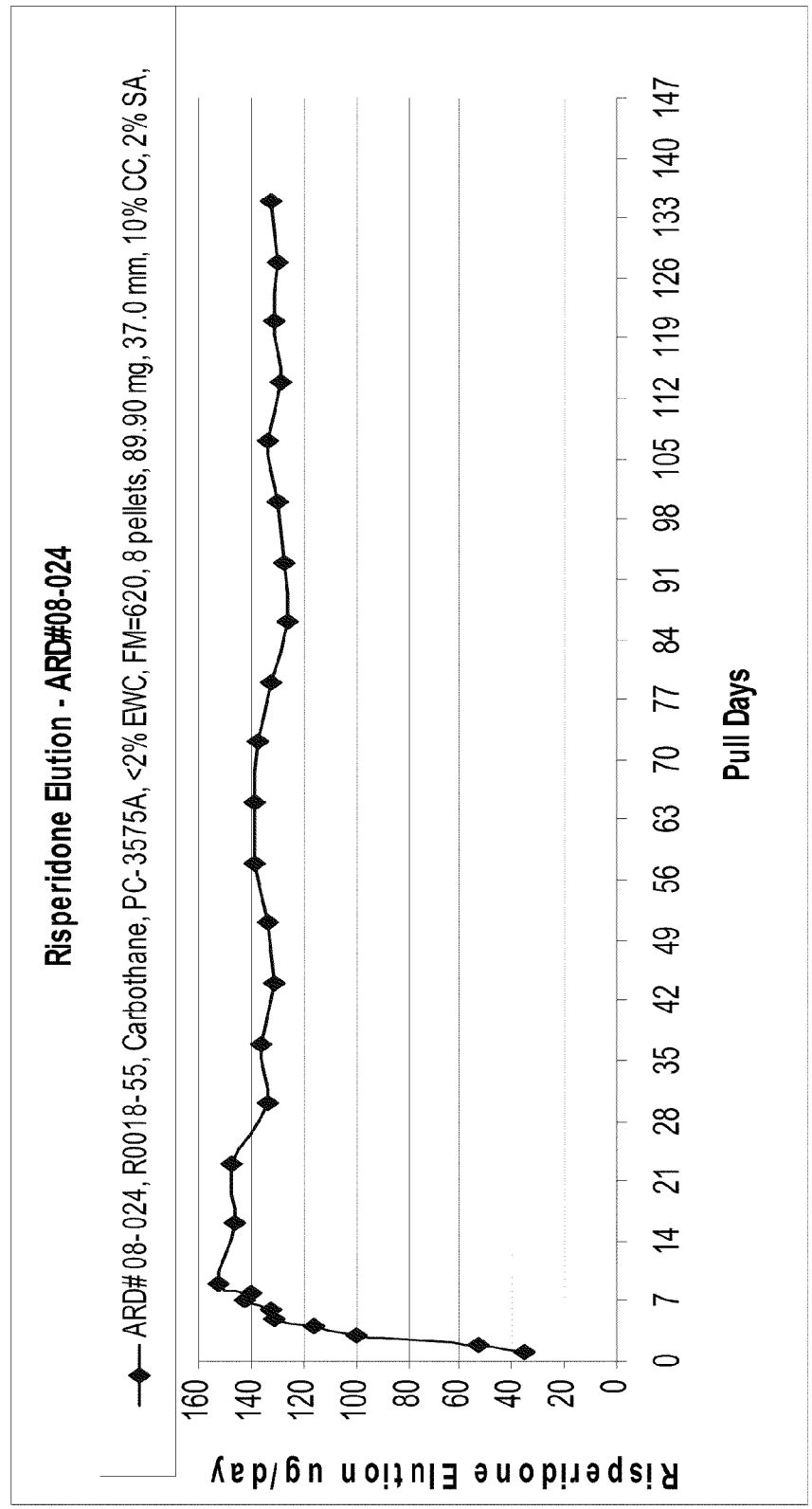
FIG. 8 is a graph of the release rate of risperidone from Carbothane® PC-3575A polyurethane implants (Flex Modulus 620 psi) that served as in vitro controls for implants used in the beagle dog study described in Example 8. The in vitro elution study of these implants was initiated on the date of implantation of the subject implants as part of an assessment of in vivo-in vitro correlation.

Release rates were compared for risperidone from Tecoflex® EG-80A polyurethane implants (F.M. 1000 psi) and two grades of Tecophilic® polyurethane implants, HP-60D-35 and HP-60D-60 (EWC, 23.6% and 30.8%, respectively) (FIG. 8). All were sampled weekly for 10 weeks. All implants were of equivalent geometry and drug load.

Release rates were obtained for risperidone from Carbothane® PC-3575A polyurethane implants (F.M. 620 psi) that served as in vitro controls for implants used in the beagle dog study described in Example 4. The in vitro elution study of these implants was initiated on the date of implantation of the subject implants as part of an assessment of in vivo-in vitro correlation.

Example 4

Evaluation of Polyurethane Subcutaneous Implant Devices Containing Risperidone in Beagle Dogs This study determines the blood levels of risperidone from one or two implants and the duration of time the implants release the drug. Polyurethane-based implantable devices comprising a pellet comprising risperidone were implanted into beagles to determine release rates of risperidone in vivo. The results of the sample analysis are summarized in Table 3 and FIG. 10. Risperidone is still present at a high level in the dog plasma at the end of the third month. The study was conducted in accordance with WCFP's standard operating procedures (SOPs), the protocol, and any protocol amendments. All procedure were conducted in accordance with the Guide for the Care and Use of Laboratory Animals (National Research Center, National Academy Press, Washington, D.C., 1996), and approved by the Institutional Animal Care and Use Committee in WCFP.

The implants initially contained about 80 mg of risperidone and are designed to deliver approximately 130 mcg/day for 3 months. The test article was stored at between 2-8° C. before use.

The animals were as follows:
Species: Canine
Strain: Beagle dog
Source: Guangzhou Pharm. Industril Research Institute,
Certification No: SCXK(YUE)2003-0007
Age at Initiation of Treatment: 6~9 months
Weight: 8~10 kg
Number and Sex: 6 males Prior to study initiation, animals were assigned a pretreatment identification number. All animals were weighed before administration once weekly, and received cage-side observations daily by qualified veterinarian during acclimation period. All animals were given a clinical examination prior to selection for study. Animals with any evidence of disease or physical abnormalities were not selected for study. The blood sampling was taken as Baseline at the 3rd and 2nd day before implant. Animals were then randomized into to 2 groups, with the dosing schedule provided as follows:

| Group | Dose Route | No. of Animals Male | Dose rate (mcg/day) | Total Dose (mg) |
|---|---|---|---|---|
| 1 | Subcutaneous implant | 3 | 130 | 23 (single implant) |
| 2 | Subcutaneous implant | 3 | 260 | 46 (double implants) |

Each animal was anesthetized by general anesthesia via pentobarbital sodium at the dose of 30 mg/kg for device implantation. The drug was released at a steady rate for several months. Half the animals received one implant (group 1) and the others received two implants (group 2). A 5 cm2 area of the shoulder was shaved and 2 mL of marcaine infused under the skin to numb the area. A small incision was made on the shoulder and the device was slid under the skin. The small incision was closed and the animal was allowed to recover and return to his run. Over the next five to seven days, the implantation site was be monitored for signs of infection or reaction. The skin staples were removed when the skin has healed sufficiently. At the end of three months, the devices were removed, just as they would clinically.

Animals were fasted at least four hours prior to blood sampling. Since blood sampling was done in the morning, food was withheld overnight. Blood samples were drawn using a 20 G needle and collected directly into the 5 mL tubes containing sodium heparin and maintained chilled until centrifugation. Samples were then centrifuged at 5000 RPM for 5 minutes at 4° C. The separated plasma was then be transferred into two 3 mL cryo tubes. The samples were labeled with the actual date the sample was taken, the corresponding study day, the dog identification and the duplicate sample designator (either A or B). Samples were kept at −20° C. until ready for analysis.

On two consecutive days, prior to implantation of the delivery device, baseline blood samples were taken. In addition, daily blood samples were taken during the first week and weekly blood samples were taken for the three months following implantation. Two 5 mL blood samples were drawn at each time from each dog. Blood samples were drawn from the cephalic veins primarily; with the saphenous or jugular used as a backup. For both the single and double implant groups, blood samples were drawn at appropriate times as outlined in Table 3 below. Analysis required at least 2 mL of plasma, which required no less than 10 mL of blood drawn for each sample. Analysis of plasma concentrations of risperidone was performed using an LC/MS assay developed for this compound. A single assay was be run for each sample. Samples were collected, held at the appropriate condition and analyzed in batches.

TABLE 3

Concentration of Risperidone in Dog Plasma

| | | | Group 1 (single implant) | | | Group 2 (double implants) | | | Group 1 | | Group 2 | |
|---|---|---|---|---|---|---|---|---|---|---|---|---|
| Date | Week | Day | 1M01 | 1M02 | 1M03 | 2M01 | 2M02 | 2M03 | Mean | S.D. | Mean | S.D. |
| | | −3 | — | — | — | — | — | — | | | | |
| | | −2 | — | — | — | — | — | — | | | | |

TABLE 3-continued

Concentration of Risperidone in Dog Plasma

| | | | Group 1 (single implant) | | | Group 2 (double implants) | | | Group 1 | | Group 2 | |
|---|---|---|---|---|---|---|---|---|---|---|---|---|
| Date | Week | Day | 1M01 | 1M02 | 1M03 | 2M01 | 2M02 | 2M03 | Mean | S.D. | Mean | S.D. |
| 1.29 | 1 | 1 | BLQ | BLQ | 0.26 | BLQ | 0.54 | BLQ | 0.26 | / | 0.54 | / |
| 1.30 | 1 | 2 | 0.77 | BLQ | 0.24 | 0.53 | 1.86 | 0.46 | 0.51 | 0.37 | 0.95 | 0.79 |
| 1.31 | 1 | 3 | 1.16 | 0.78 | 0.37 | 1.15 | 2.70 | 0.92 | 0.77 | 0.40 | 1.59 | 0.97 |
| 2.01 | 1 | 4 | 1.26 | 0.79 | 0.66 | 1.21 | 3.85 | 0.94 | 0.90 | 0.32 | 2.00 | 1.61 |
| 2.02 | 1 | 5 | 1.15 | 0.66 | 1.03 | 1.02 | 3.13 | 0.77 | 0.95 | 0.26 | 1.64 | 1.30 |
| 2.03 | 1 | 6 | 1.14 | 0.58 | 0.52 | 0.97 | 2.96 | 0.79 | 0.75 | 0.34 | 1.57 | 1.20 |
| 2.04 | 1 | 7 | 1.17 | 0.72 | 0.44 | 0.89 | 3.27 | 0.73 | 0.78 | 0.37 | 1.63 | 1.42 |
| 2.11 | 2 | 14 | 1.26 | 1.03 | 0.38 | 1.15 | 2.81 | 1.01 | 0.89 | 0.46 | 1.66 | 1.00 |
| 2.18 | 3 | 21 | 1.09 | 0.70 | 0.62 | 1.38 | 3.09 | 0.91 | 0.80 | 0.25 | 1.79 | 1.15 |
| 2.25 | 4 | 28 | 1.34 | 0.84 | 1.02 | 1.71 | 3.55 | 1.10 | 1.07 | 0.25 | 2.12 | 1.28 |
| 3.03 | 5 | 35 | 2.07 | 2.23 | 1.65 | 1.97 | 4.54 | 1.12 | 1.98 | 0.30 | 2.54 | 1.78 |
| 3.10 | 6 | 42 | 1.53 | 1.13 | 1.87 | 1.86 | 3.34 | 1.40 | 1.51 | 0.37 | 2.20 | 1.01 |
| 3.17 | 7 | 49 | 1.33 | 1.09 | 1.16 | 1.67 | 2.23 | 1.29 | 1.19 | 0.12 | 1.73 | 0.47 |
| 3.24 | 8 | 56 | 1.56 | 1.29 | 1.30 | 1.28 | 2.09 | 1.54 | 1.38 | 0.15 | 1.64 | 0.41 |
| 3.31 | 9 | 63 | 1.06 | 0.83 | 1.39 | 1.13 | 2.27 | 0.97 | 1.09 | 0.28 | 1.46 | 0.71 |
| 4.07 | 10 | 70 | 1.39 | 1.00 | 1.36 | 1.42 | 3.51 | 1.48 | 1.25 | 0.22 | 2.14 | 1.19 |
| 4.14 | 11 | 77 | 1.23 | 1.15 | 1.41 | 1.61 | 3.47 | 1.07 | 1.26 | 0.13 | 2.05 | 1.26 |
| 4.21 | 12 | 84 | 1.29 | 1.10 | 1.21 | 1.23 | 3.47 | 1.23 | 1.20 | 0.10 | 1.98 | 1.29 |
| 4.28 | 13 | 91 | 1.38 | 0.88 | 1.10 | 1.09 | 3.22 | 1.38 | 1.12 | 0.25 | 1.90 | 1.16 |
| 5.05 | 14 | 98 | 1.94 | 1.01 | 1.32 | 1.28 | 3.76 | 1.19 | 1.42 | 0.47 | 2.08 | 1.46 |
| 5.12 | 15 | 105 | 1.54 | 0.98 | 1.23 | 1.37 | 3.48 | 1.31 | 1.25 | 0.28 | 2.05 | 1.24 |
| 5.19 | 16 | 112 | 1.61 | 0.94 | 1.30 | 1.22 | 3.98 | 1.59 | 1.28 | 0.34 | 2.26 | 1.50 |
| 5.26 | 17 | 119 | 1.36 | 0.97 | 1.49 | 1.48 | 2.66 | 1.65 | 1.27 | 0.27 | 1.93 | 0.64 |
| 6.02 | 18 | 126 | 1.40 | 0.93 | 0.95 | 0.99 | 3.25 | 1.16 | 1.09 | 0.27 | 1.80 | 1.26 |
| 6.09 | 19 | 133 | 1.47 | 1.19 | 1.33 | 1.36 | 3.36 | 0.98 | 1.33 | 0.14 | 1.90 | 1.28 |
| 6.16 | 20 | 140 | 1.16 | 1.25 | 0.85 | 3.2* | 3.46 | 1.03 | 1.09 | 0.21 | 2.25 | 1.72 |
| 6.23 | 21 | 147 | 1.16 | 1.23 | 1.26 | 1.17 | 5.56 | 1.53 | 1.22 | 0.05 | 2.75 | 2.44 |
| 6.30 | 22 | 154 | 1.63 | 2.02* | 1.44 | 1.41 | 5.21 | 1.34 | 1.54 | 0.13 | 2.65 | 2.21 |
| 7.07 | 23 | 161 | 1.26 | 1.04 | 0.92 | 1.41 | 44.82** | 1.36 | 1.07 | 0.17 | 1.39 | 0.04 |
| 7.14 | 24 | 168 | 1.85 | 0.9 | BLQ | 1.5 | 3.78 | 1.26 | 1.38 | 0.67 | 2.18 | 1.39 |
| 7.21 | 25 | 175 | 1.69 | 1 | BLQ | 1.29 | 3.46 | 1.3 | 1.35 | 0.49 | 2.02 | 1.25 |
| 7.28 | 26 | 182 | 1.42 | 1.09* | 0.34 | 1.7 | 4.48 | 1.82 | 0.88 | 0.76 | 2.67 | 1.57 |

*re-analysis
**re-analysis, abnormal data

Figure 9:
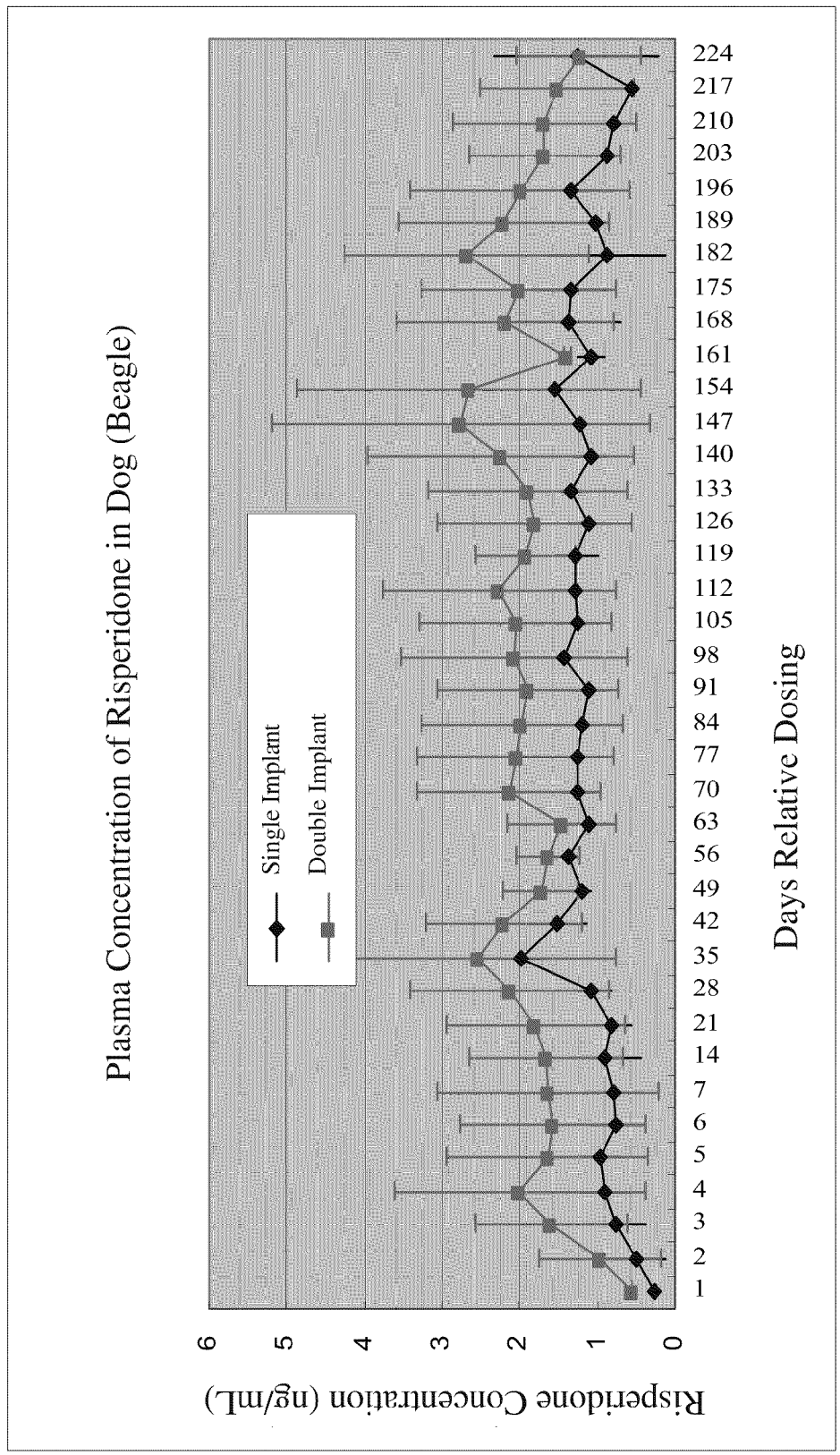
FIG. 9 is a graph of the in vivo plasma concentration of risperidone in the beagle dog study described in Example 8. The lower plot represents the average plasma concentration achieved in dogs implanted with one Carbothane® PC-3575A polyurethane implant (Flex Modulus 620 psi). The upper plot represents the average plasma concentration achieved in dogs implanted with two Carbothane® PC-3575A polyurethane implants (Flex Modulus 620 psi).
Figure 10:
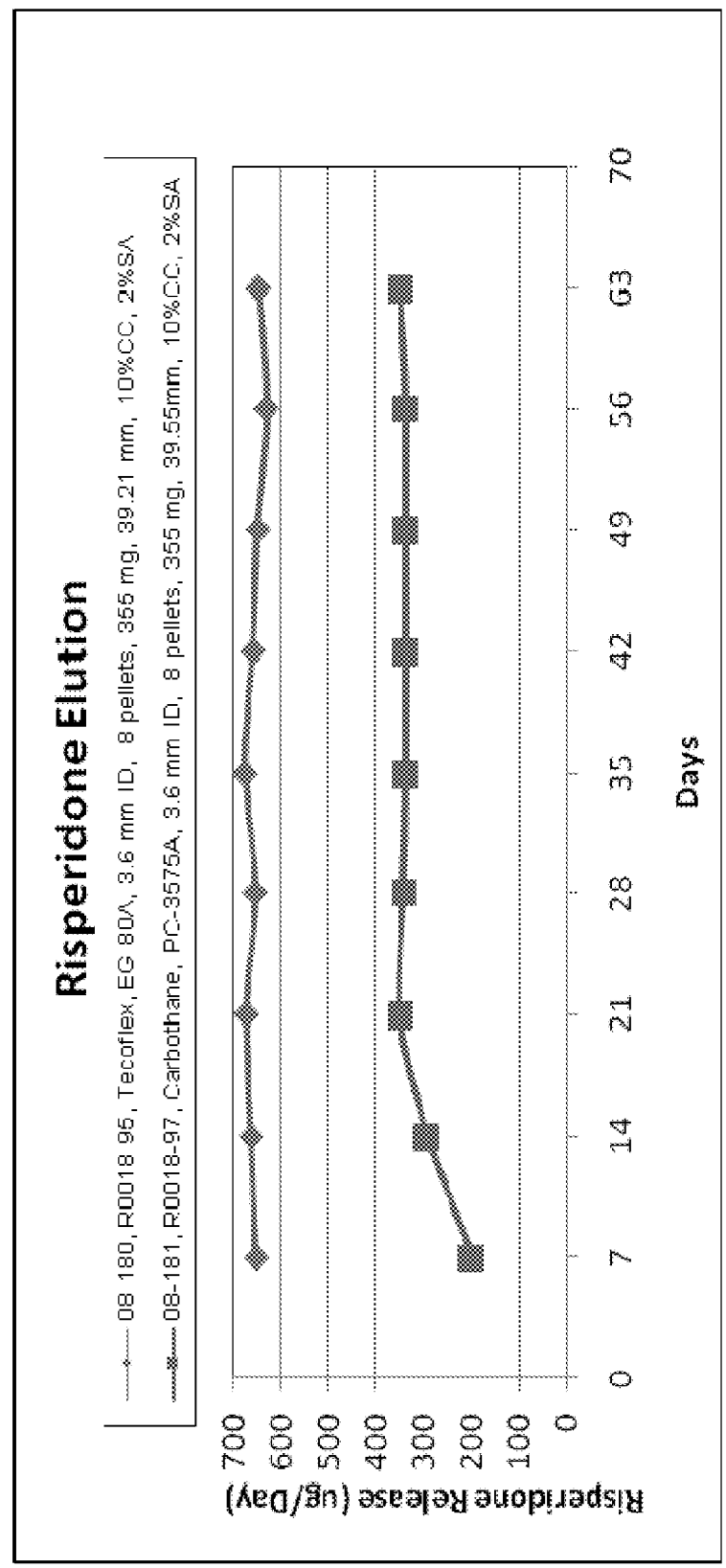
FIG. 10 is a graph showing the in vitro release of risperidone from Tecoflex® and Carbothane® implants. The pellets comprising the risperidone formulation had a diameter of 3.5 mm, a length of about 4.5 mm and a weight of 5.4 mg. The implant had a reservoir length of about 39-40 mm, a wall thickness of 0.2 mm, and internal diameter of 3.6 mm and an overall length of about 45 mm.

FIG. 9 is a graph of the in vivo plasma concentration of risperidone in the beagle dog study. The lower plot represents the average plasma concentration achieved in dogs implanted with one Carbothane® PC-3575A polyurethane implant (F.M. 620 psi). The upper plot represents the average plasma concentration achieved in dogs implanted with two Carbothane® PC-3575A polyurethane implants (F.M. 620 psi).

Example 5

Figure 11:
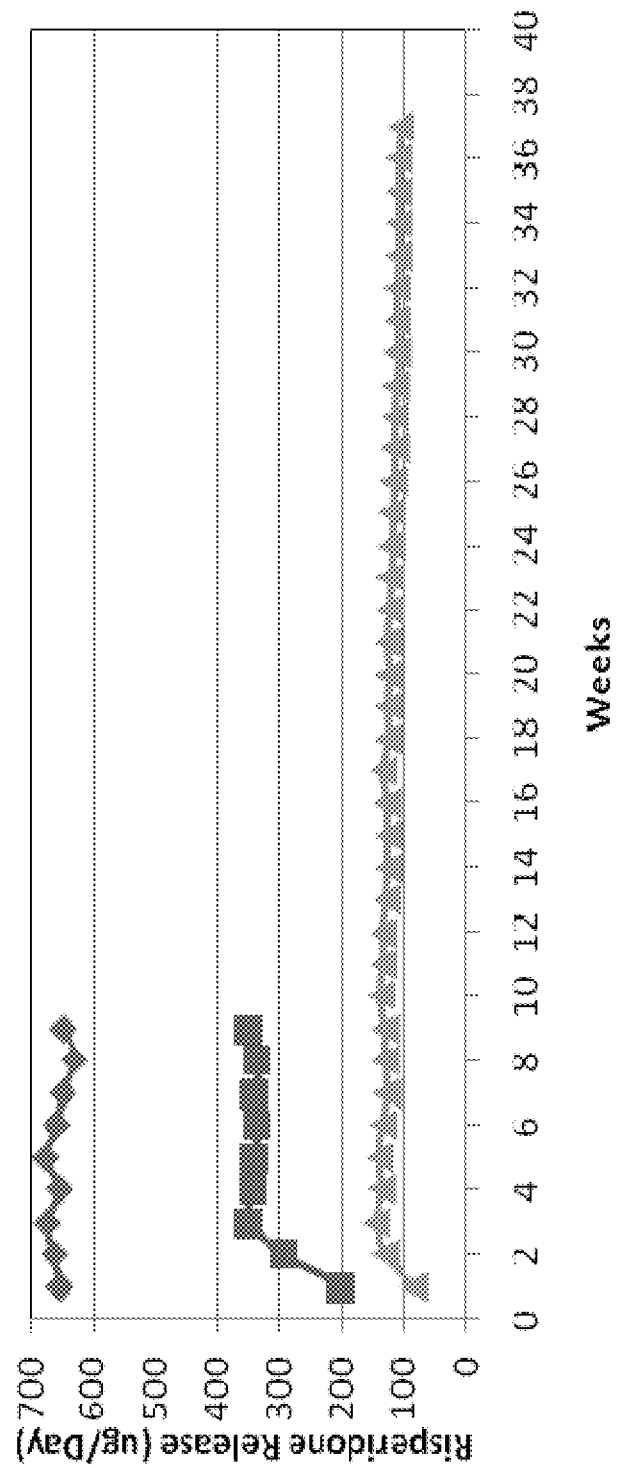
FIG. 11 is a graph showing the in vivo release of risperidone from Tecoflex® and Carbothane® implants, as compared to a control. The pellets comprising the risperidone formulation had a diameter of 3.5 mm, a length of about 4.5 mm and a weight of 5.4 mg. The implant had a reservoir length of about 39-40 mm, a wall thickness of 0.2 mm, and internal diameter of 3.6 mm and an overall length of about 45 mm.

Evaluation of Polyurethane Subcutaneous Implant Devices Containing Risperidone in Beagle Dogs Expanding on the data presented in Example 4, this study determines the blood levels of risperidone from one or two larger implants and the duration of time the implants release the drug. Polyurethane-based implantable devices comprising a pellet comprising risperidone were implanted into beagles to determine release rates of risperidone in vivo. The results of the larger implant data are summarized in FIG. 10 (in vitro elution profile) and FIG. 11 (elution in beagle dogs).

The pellets comprising the risperidone formulation used for this study had a diameter of 3.5 mm, a length of about 4.5 mm and a weight of 5.4 mg. The implant had a reservoir length of about 39-40 mm, a wall thickness of 0.2 mm, and internal diameter of 3.6 mm and an overall length of about 45 mm. initially contained about 80 mg of risperidone and are designed to deliver approximately 130 mcg/day for 3 months.

Equivalents

The present disclosure is not to be limited in terms of the particular embodiments described in this application, which are intended as illustrations of various aspects. Many modifications and variations can be made without departing from the spirit and scope of the disclosure, as will be apparent to those skilled in the art. Functionally equivalent methods, systems, and apparatus within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting. As will be understood by one skilled in the art, for any and all purposes, such as in terms of providing a written description, all ranges disclosed herein also encompass any and all possible subranges and combinations of subranges thereof.

While various aspects and embodiments have been disclosed herein, other aspects and embodiments will be apparent to those skilled in the art. All references cited herein are incorporated by reference in their entireties.

What is claimed is:

1. A drug delivery device for the controlled release of risperidone over an extended period of time to produce local or systemic pharmacological effects, comprising:

a) a polyurethane-based polymer formed to define a hollow space; and
a solid drug formulation consisting essentially of a formulation consisting essentially of risperidone and optionally one or more pharmaceutically acceptable carriers, wherein the solid drug formulation is contained in the hollow space, and wherein the device provides a pre-determined release rate of risperidone from the device after implantation and wherein the polyurethane-based polymer is formed from one or more polyols, wherein the general polyol structure is selected from the group consisting of:
—[O—(CH$_2$)$_n$]$_x$—O—;
O—(CH$_2$—CH$_2$—CH$_2$—CH$_2$)$_x$—O—; and
O—[(CH$_2$)$_6$—CO$_3$]$_n$—(CH$_2$)—O—.

2. The drug delivery device of claim 1, wherein the drug delivery device is conditioned and primed under conditions chosen to be consistent with the water solubility characteristics of the risperidone.

3. The drug delivery device of claim 2 including one or more pharmaceutically acceptable carriers, and wherein the pharmaceutically acceptable carrier is stearic acid.

4. The drug delivery device of claim 1, wherein the polyol comprises —[)—(CH$_2$)$_n$]$_x$—O—, and wherein the polyurethane-based polymer has an equilibrium water content of between about 5% and about 200%.

5. The drug delivery device of claim 4, wherein the polyurethane-based polymer has an equilibrium water content of at least about 15%.

6. The drug delivery device of claim 1, wherein risperidone is released at a zero-order rate of about 149 μg/day per square centimeter of the surface area of the implantable device.

7. The drug delivery device of claim 1, wherein the polyol comprises O—(CH$_2$—CH$_2$—CH$_2$—CH$_2$)$_x$—O—, and wherein the polyurethane-base polymer has a flex modulus of between about 1000 and about 92,000 psi.

8. The drug delivery device of claim 7, wherein the polyurethane-based polymer has a flex modulus of about 2,300 psi.

9. The drug delivery device of claim 7, wherein risperidone is released at a zero-order rate of about 146 μg/day per square centimeter of the surface area of the implantable device.

10. The drug delivery device of claim 1, wherein the polyol comprises O—[(CH$_2$)$_6$—CO$_3$]$_n$—(CH$_2$)—O—, and wherein the polyurethane-based polymer has a flex modulus of between about 620 and about 92,000 psi.

11. The drug delivery device of claim 10, wherein the polyurethane-based polymer has a flex modulus of about 620 psi.

12. The drug delivery device of claim 10, wherein risperidone is released at a zero-order rate of about 40 μg/day per square centimeter of the surface area of the implantable device.

13. The drug delivery device of claim 1, wherein appropriate conditioning and priming parameters are selected to establish the predetermined delivery rates of the risperidone, wherein the priming parameters are time, temperature, conditioning medium and priming medium.

14. The drug delivery device of claim 7, wherein the polyurethane-based polymer has a flex modulus of about 1000 psi.

15. The drug delivery device of claim 1 including the one or more pharmaceutically acceptable carriers, and wherein the one or more pharmaceutically acceptable carriers comprise stearic acid.

16. The drug delivery device of claim 7 including the one or more pharmaceutically acceptable carriers, and wherein the one or more pharmaceutically acceptable carriers comprise stearic acid.

17. The drug delivery device of claim 16, wherein the stearic acid comprises about 2 wt % of the solid drug formulation.

18. The drug delivery device of claim 17, wherein the polyurethane-based polymer has a flex modulus of about 1000 psi.

19. The drug delivery device of claim 1, with an internal diameter of about 3.6 mm.

20. The drug delivery device of claim 1, which has a length of about 7.5 mm to about 50 mm.

21. The drug delivery device of claim 7, which has a length of about 7.5 mm to about 50 mm.

22. The drug delivery device of claim 1, which has a length of about 45 mm.

23. The drug delivery device of claim 1, wherein the polyurethane-based polymer formed to define a hollow space has a wall thickness of 0.2 mm.

24. The drug delivery device of claim 1, wherein the device provides a pre-determined release rate of risperidone of between about 0.001 mg/day to about 15 mg/day from the device after implantation.

25. The drug delivery device of claim 7, wherein the device provides a pre-determined release rate of risperidone of between about 0.001 mg/day to about 15 mg/day from the device after implantation.

26. The drug delivery device of claim 1, wherein the general polyol structure is: —[O—(CH$_2$)$_n$]$_x$—O—.

27. The drug delivery device of claim 12, wherein the general polyol structure is: O—(CH$_2$—CH$_2$—CH$_2$—CH$_2$)$_x$—O—.

28. The drug delivery device of claim 1, wherein the general polyol structure is: O—[(CH$_2$)$_6$—CO$_3$]$_n$—(CH$_2$)—O—.

29. A method for delivering an effective amount of risperidone to a subject, comprising implanting the drug delivery device of claim 1 into the subject.

30. The method of claim 29, wherein the polyol comprises —[O—(CH$_2$)$_n$]$_x$—O—, and wherein the polyurethane-based polymer has an equilibrium water content of between about 5% and about 200%.

31. The method of claim 30, wherein the polyurethane-based polymer has an equilibrium water content of at least about 15%.

32. The method of claim 29, wherein risperidone is released at a zero-order rate of about 149 μg/day per square centimeter of the surface area of the implantable device.

33. The method of claim 29, wherein the polyol comprises O—(CH$_2$—CH$_2$—CH$_2$—CH$_2$)$_x$—O—, and wherein the polyurethane-base polymer has a flex modulus of between about 1000 and about 92,000 psi.

34. The method of claim 33, wherein the polyurethane-based polymer has a flex modulus of about 2,300 psi.

35. The method of claim 33, wherein risperidone is released at a zero-order rate of about 146 μg/day per square centimeter of the surface area of the implantable device.

36. The method of claim 29, wherein the polyol comprises O—[(CH$_2$)$_6$—CO$_3$]$_n$—(CH$_2$)—O—, and wherein the polyurethane-based polymer has a flex modulus of between about 620 and about 92,000 psi.

37. The method of claim 36, wherein the polyurethane-based polymer has a flex modulus of about 620 psi.

38. The method of claim 36, wherein risperidone is released at a zero-order rate of about 40 μg/day per square centimeter of the surface area of the implantable device.

\* \* \* \* \*

UNITED STATES PATENT AND TRADEMARK OFFICE
CERTIFICATE OF CORRECTION

| | | |
|---|---|---|
| PATENT NO. | : 9,078,900 B2 | Page 1 of 1 |
| APPLICATION NO. | : 12/569558 | |
| DATED | : July 14, 2015 | |
| INVENTOR(S) | : Kuzma et al. | |

It is certified that error appears in the above-identified patent and that said Letters Patent is hereby corrected as shown below:

In the claims

Claim 1, column 19, lines 3-5, "a solid drug formulation consisting essentially of a formulation consisting essentially of risperidone and optionally one or more pharmaceutically acceptable carriers" should read --b) a solid drug formulation consisting essentially of a formulation consisting essentially of risperidone and optionally one or more pharmaceutically acceptable carriers--

Signed and Sealed this
Fifth Day of January, 2016

Michelle K. Lee
*Director of the United States Patent and Trademark Office*